(12) United States Patent
Damadian et al.

(10) Patent No.: US 6,369,571 B1
(45) Date of Patent: Apr. 9, 2002

(54) MRI APPARATUS

(75) Inventors: Jevan Damadian, East Northport; John Linardos, Smithtown; Gordon T. Danby, Wading River; Raymond V. Damadian, Woodbury, all of NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 09/852,569

(22) Filed: May 10, 2001

Related U.S. Application Data

(60) Division of application No. 09/200,099, filed on Nov. 25, 1998, which is a continuation-in-part of application No. 08/978,084, filed on Nov. 25, 1997, now abandoned, which is a continuation-in-part of application No. 08/975,913, filed on Nov. 21, 1997, now Pat. No. 6,201,394, which is a continuation-in-part of application No. 07/993,072, filed on Dec. 18, 1992, now Pat. No. 6,023,165.

(51) Int. Cl.⁷ .................................. G01V 3/00
(52) U.S. Cl. ...................... 324/318; 324/319
(58) Field of Search ............... 324/318, 319, 324/320, 322, 300, 307, 309; 335/299

(56) References Cited

U.S. PATENT DOCUMENTS

| | | |
|---|---|---|
| 4,407,292 A | 10/1983 | Edrich |
| 4,534,358 A | 8/1985 | Young |
| 4,608,991 A | 9/1986 | Rollwitz |
| 4,613,820 A | 9/1986 | Edelstein et al. |
| 4,629,989 A | 12/1986 | Riehl et al. |
| 4,641,119 A | 2/1987 | Moore |
| 4,644,275 A | 2/1987 | Young |
| 4,668,915 A | 5/1987 | Daubin et al. |
| 4,672,346 A | 6/1987 | Miyamoto et al. |
| 4,679,022 A | 7/1987 | Miyamoto et al. |
| 4,707,663 A | 11/1987 | Minkoff et al. |
| 4,728,895 A * | 3/1988 | Briguet et al. ............. 324/318 |
| 4,766,378 A | 8/1988 | Danby et al. |
| 4,770,182 A | 9/1988 | Damadian et al. |
| 4,777,464 A | 10/1988 | Takabatashi et al. |
| 4,829,252 A | 5/1989 | Kaufman |
| 4,920,318 A | 4/1990 | Misic et al. |
| 4,924,198 A | 5/1990 | Laskaris |
| 4,943,774 A | 7/1990 | Breneman et al. |
| 4,968,937 A | 11/1990 | Akgun |
| D313,073 S | 12/1990 | Kaufman et al. |
| 4,985,678 A | 1/1991 | Gangarosa et al. |
| 5,050,605 A | 9/1991 | Eydelman et al. |
| 5,065,701 A | 11/1991 | Pell |
| 5,124,651 A | 6/1992 | Danby et al. |
| 5,134,374 A | 7/1992 | Breneman et al. |
| 5,153,546 A | 10/1992 | Laskaris |
| 5,180,982 A * | 1/1993 | Zeiger ........................ 324/322 |

(List continued on next page.)

FOREIGN PATENT DOCUMENTS

| | | |
|---|---|---|
| DE | 3140225 A1 | 4/1983 |
| JP | 62-26052 | 2/1987 |
| JP | 4-332531 | 11/1992 |

*Primary Examiner*—Louis Arana
(74) *Attorney, Agent, or Firm*—Lerner, David, Littenberg, Krumholz & Mentlik, LLP

(57) ABSTRACT

A magnet for magnetic resonance imaging has an interior working space within the magnet frame sufficient to accommodate a physician and a patient. Because the physician is positioned inside the magnet frame, the physician has unimpeded access to the patient. Elements of the magnet frame desirably encompass a room, and the magnet frame may be concealed from view of a patient within the room. Preferred embodiments facilitate MRI imaged guided surgery and other procedures performed while the patient is being imaged, and minimize claustrophobia experienced by the patient. Also provided is a magnet having field coils disposed about the of pole portions of the magnet. A diagnostic facility for high volume MRI use is also disclosed.

8 Claims, 22 Drawing Sheets

U.S. PATENT DOCUMENTS

| | | |
|---|---|---|
| 5,194,810 A | 3/1993 | Breneman et al. |
| 5,197,474 A | 3/1993 | Englund et al. |
| 5,207,224 A | 5/1993 | Dickinson et al. |
| 5,211,165 A | 5/1993 | Dumoulin et al. |
| 5,229,723 A | 7/1993 | Sakurai et al. |
| 5,250,901 A | 10/1993 | Kaufman et al. |
| 5,304,932 A | 4/1994 | Carlson |
| 5,305,749 A | 4/1994 | Li et al. |
| 5,315,276 A | 5/1994 | Huson et al. |
| 5,382,904 A | 1/1995 | Pissanetzky |
| 5,382,905 A | 1/1995 | Miyata et al. |
| 5,412,363 A | 5/1995 | Breneman et al. |
| 5,436,607 A | 7/1995 | Chari et al. |
| 5,490,513 A | 2/1996 | Damadian et al. |
| 5,519,372 A | 5/1996 | Palkovich et al. |
| 5,754,085 A | 5/1998 | Danby et al. |
| 6,054,854 A * | 4/2000 | Kawamoto .................. 324/318 |
| 6,201,394 B1 | 3/2001 | Danby et al. ................ 324/319 |
| 6,208,144 B1 | 3/2001 | McGinley et al. .......... 324/319 |

* cited by examiner

MRI APPARATUS

CROSS REFERENCE TO RELATED APPLICATION

The present application is a divisional of U.S. patent application Ser. No. 09/200,099, filed Nov. 25, 1998, which is a continuation-in-part of U.S. patent application Ser. No. 08/975,913, filed Nov. 21, 1997 now U.S. Pat. No. 6,201, 394, which is a continuation-in-part of U.S. patent application Ser. No. 07/993,072, filed Dec. 18, 1992 now U.S. Pat. No. 6,023,165, the disclosures of which are hereby incorporated by reference herein. U.S. patent application Ser. No. 08/975,913 is also a continuation-in-part of U.S. patent application Ser. No. 08/978,084, filed Nov. 25, 1997, the disclosure of which is also incorporated by reference herein.

BACKGROUND OF THE INVENTION

The present invention relates to magnetic resonance imaging or "MRI".

MRI is widely used in medical and other arts to obtain images of a subject such as a medical patient. The patient's body is placed within a subject-receiving space of a primary field magnet and exposed to a strong, substantially constant primary magnetic field. The atomic nuclei spin around axes aligned with the magnetic field. Powerful radio frequency "RF" signals are broadcast into the subject-receiving space to excite atomic nuclei within the patient's body into a resonance state in which the spinning nuclei generate minuscule RF signals. These signals are referred to herein as magnetic resonance signals. Magnetic field gradients are applied so that the magnitude of the magnetic field varies with location inside the subject-receiving space. As a result, characteristics of the magnetic resonance signals from different locations within the region, such as the frequency and phase of the signals, can be made to vary in a predictable manner, depending upon position within the region. Thus, the magnetic resonance signals are "spatially encoded" so that it is possible to distinguish between signals from different parts of the region. After repeating this procedure with various different gradients, it is possible to derive a map showing the intensity or other characteristics of the magnetic resonance signals versus position within the excited region. Because these characteristics vary with concentration of different chemical substances and other characteristics of the tissue within the subject's body, different tissues provide different magnetic resonance signal characteristics. When the map of the magnetic resonance signal characteristics is displayed in a visual format, such as on screen or on a printed image, the map forms a visible picture of structures within the patient's body.

MRI provides unique imaging capabilities which are not attainable from any other imaging method. For example, MRI can provide vivid, detailed images of soft tissues, including abnormalities such as tumors, and other structures which cannot be seen readily in X-ray images. Moreover, MRI operates without exposing the patient or the physician to ionizing radiation such as X-rays. For these and other reasons, MRI is widely utilized in medicine.

Some of the primary field magnets utilized heretofore have imposed severe physical constraints on the patient and on medical personnel attending to the patient during the MRI procedure. For example, conventional solenoidal primary field magnets use a series of circular superconducting coils spaced apart from one another along an axis. These magnets provide a small, tubular subject-receiving space enclosed within the solenoids. A patient to be imaged must slide into the tubular space. The experience may be highly claustrophobic. Some obese or pregnant patients often cannot fit inside the patient-receiving space. Moreover, it is essentially impossible for a physician or technician to reach those regions of the patient disposed inside the subject-receiving space.

Attempts have been made heretofore to create "open" MRI primary field magnets using ferromagnetic frames. Although these designs provide somewhat better access to the patient for certain diagnostic scanning, and a somewhat less claustrophobic experience for the patient, they are less than optimal for surgical intervention or physician/technician-assisted diagnostic procedures. For example, these designs provide limited access of physicians, surgeons, or technicians, to the patient. Additionally, the designs have difficulty providing a highly uniform field with pole dimensions desirable for surgery or diagnostic purposes.

As described, for example, in commonly assigned U.S. Pat. No. 4,707,663, other primary field magnets utilize ferromagnetic frames to route and concentrate magnetic flux into the patient-receiving space. Primary field magnets using such a ferromagnetic frame can employ permanent magnets, resistive electromagnetic coils, or superconducting coils having a relatively low number of ampere-turns while still providing a high field strength in the patient-receiving space. Moreover, such magnet assemblies can provide excellent field uniformity. Ferromagnetic frame magnets in accordance with the '663 patent also provide a less claustrophobic, more accessible subject-receiving space.

As disclosed in co-pending, commonly assigned U.S. patent application Ser. No. 07/952,810 filed Sep. 28, 1992, now U.S. Pat. No. 5,754,085 the disclosure of which is hereby incorporated by reference herein, a ferromagnetic magnetic frame may include a pair of plate-like pole supports spaced apart from one another and supported above one another by a set of columns. In preferred magnets according to the '085 patent, the frame defines a polar axis passing through the space between the pole supports. Preferably, ferromagnetic poles project from the pole supports adjacent the polar axis, so that the poles define a subject-receiving space at a medial plane, midway between the plates. The columns have unique shapes such that, in preferred embodiments, the columns flare outwardly in the radial direction, away from the polar axis adjacent the medial plane. The dimensions of each column in the circumferential direction, around the polar axis desirably taper so that the circumferential dimension of each column is at a minimum in a region adjacent the medial plane. As described in further detail in the '085 patent, magnets with ferromagnetic frames in accordance with preferred embodiments of the invention taught therein can provide a unique combination of accessibility and a large, aesthetically pleasing, and non-claustrophobic, patient-receiving space and can also provide high field strength without resort to superconducting coils. Even higher field strengths can be provided where superconducting coils are used.

Magnets according to preferred embodiments taught in the '085 patent thus provide an elegant solution to the problems of claustrophobia, lack of access and limitations on field strength and uniformity posed by prior designs. Surgical operations and other medical procedures can be performed readily on a patient while the patient is disposed inside the patient-receiving space of preferred magnets according the '085 patent. The ability to perform surgical operations while the patient is disposed inside the patient-receiving space allows the physician to treat the patient under direct guidance of a MRI image acquired during the procedure itself. For example, as the surgeon advances a probe into the body to treat a lesion, the surgeon can see the probe and the lesion in the MRI image.

However, even with this enhanced design, the patient still perceives the MRI procedure as involving placement of his or her body into the interior of a machine. Moreover, the physician treating the patient still perceives that he or she must stand outside of the apparatus and reach into the apparatus to gain access to the patient. Accordingly, even further improvement in primary field magnet structures for MRI apparatus would be desirable.

SUMMARY OF THE INVENTION

One aspect of the present invention provides a magnet for magnetic resonance imaging apparatus which includes a frame. The frame desirably incorporates a pair of opposed ferromagnetic pole supports spaced apart from one another and a pair of ferromagnetic poles connected to the pole support. The poles project from the pole supports toward one another along a polar axis. The poles have distal ends remote from the pole supports. The distal ends confront one another and are spaced apart from one another by a gap distance so as to define a subject-receiving gap between the poles. The frame further includes one or more connecting elements extending between the pole supports. The connecting elements are spaced apart from the poles in a direction or directions transverse to the polar axis. The magnet further includes a source of magnetic flux adapted to direct flux through the frame so that the flux passes between the distal ends of the poles through the gap and returns through the pole supports and the connecting elements.

Most preferably, the magnet defines a working space alongside of the poles, between the pole supports and between the poles and the connecting elements sufficient to accommodate one or more adult human attendants. Thus, an attendant can be positioned inside the working space, within the magnet itself and can have access to a patient disposed in the gap between the poles. The working space desirably is about six feet or more high and about two feet or more wide, so that the attendant can work in a standing position. Most preferably, the working space extends entirely around the poles, and is unobstructed by any feature of the magnet itself. The magnet desirably includes a plurality of enclosing structures including walls, a floor and a ceiling which cooperatively define a room. The poles extend into the room, but the remainder of the frame desirably is at or outside the exterior of the room. For example, where the pole supports are spaced vertically apart from one another and the polar axis extends vertically, the poles project into the room from the floor and ceiling. Thus, the patient experiences entry into the MRI magnet as entry into a normal room with some structures extending from the floor and ceiling. Stated another way, the elements such as the connecting elements and pole supports are so far away from the patient that they do not create any feeling of claustrophobia. Because the physician or other attendant is inside the room and inside the space enclosed by the pole supports and connecting elements, these elements do not impede access by the physician or other attendant to the patient at all.

The connecting elements may be in the form of plates constituting one or more walls of the room as well as providing the pole supports which may be formed as further plates constituting the floor and ceiling of the room. The enclosing structure may further include concealment structure which conceals those parts of the frame constituting the walls from view from within the room. For example, the interior surfaces of the plates may be covered with conventional wall, floor and ceiling coverings. This contributes to the patient's belief that he or she is inside a normal room. According to further aspects of the invention, the concealment structure may include surface decoration on the surfaces bounding the room as, for example, on the walls, ceiling or floor. The magnet structure may also include pole covers covering the poles and associated structure, and the surface decoration may be provided on the pole covers as well. The surface decoration may define an outdoor scene, such as a landscape or seascape incorporating a sky region. This enhances the open, non-claustrophobic environment provided by the magnet.

Because the pole supports and connecting elements are disposed outside of the area occupied by the patient and attendant, these elements can be of essentially unlimited size. Essentially any amount of ferromagnetic material can be used to provide a low reluctance flux return path and to perform uniform distribution of flux passing to the poles. Magnets in accordance with preferred aspects of the present invention thus can provide a highly concentrated, strong magnetic field in the subject-receiving gap. Magnets according to this aspect of the invention can utilize permanent magnets, super-conducting coil or, resistive electromagnetic coils as the source of electromagnetic flux. In a particularly preferred arrangement, a coil such as a resistive electromagnetic coil encircles each pole. In systems intended to provide optimum access to the patient, for surgery or other procedures requiring considerable interaction with the patient, the coils may be disposed adjacent to the pole supports. In this configuration, the working space extends around the poles between the coils. Where the polar axis extends vertically, the working space desirably extends above one coil and below the other coil. For example, one coil may be disposed beneath the floor of the room whereas the other coil may be disposed above the ceiling.

Magnets according to a further aspect of the invention are arranged to provide optimum field uniformity. In magnets according to this aspect of the invention, the coils may extend in regions of the poles adjacent the pole tips. Thus, the coil associated with each pole may extend to within about 6 inches (15 cm) of the pole tip, and desirably to within about 3 inches (7.5 cm) of the pole tip. The coil associated with each pole may be provided as a relatively narrow toroidal solenoid in the vicinity of the pole tip or, preferably, as an elongated cylindrical solenoid surrounding the pole, the solenoid having a tip end in the vicinity of the pole tip and having a support end in the vicinity of the pole support. In these systems, the working space extends around the outside of the coil. To maintain good access to the patient, the coil desirably has a radial thickness of about 6 inches or less. Magnets according to this aspect of the invention are especially well suited to use in diagnostic procedures, including imaging without other intervention during imaging and also including interventional MRI procedures such as procedures involving the use of MRI contrast media or intrabody probes during imaging. The access to the patient provided by the magnets in accordance with this aspect of the invention also allow them to be used for surgery or other procedures requiring considerable interaction with the patient.

The gap distance between the distal ends of the pole preferably is about two feet or more. The distal ends of the poles may be either circular or non-circular. In systems intended to provide optimum access to the patient, and which employ poles with circular distal ends, the ratio between the diameter of each pole distal end and the gap distance between the poles is desirably about 2 to 1 or less. In systems designed for such optimum access where the distal ends of the poles are non-circular, the ratio between the longest dimension of each pole surface and the gap distance is desirably about 2 to 1 or less, and the ratio of the shortest dimension of each pole surface to the gap distance desirably is about 1.5:1 or less.

The magnet desirably incorporates features to further enhance field uniformity in the patient-receiving gap. Where coils are employed as the source of magnetic flux, each coil encircles the associated pole. Also, the magnet desirably includes shimming features such as shim rings, slots or other elements defining magnetic flux paths having different reluctances at different distances from the polar axis. To further promote field uniformity, each pole may include a pole tip defining a distal end of the pole and a pole stem extending from the proximal end of the pole to the pole tip. The flux source is arranged to direct the flux in a forward direction through each pole. The magnet may include bucking magnets surrounding the pole stem. The stem bucking magnets desirably provide flux directed in a reversed direction opposite to the forward direction. This tends to minimize leakage of flux from the pole stems to the connecting elements. The relatively large spacing between the poles and the connecting elements in radial directions transverse to the polar axis helps to minimize flux leakage from the poles, so that a very large portion of the flux tends to pass between the poles. This further promotes flux uniformity and a strong field in the subject-receiving gap.

In a particularly preferred arrangement, the vertical connecting elements are disposed at least about 7 feet from the polar axis. Thus, a typical human patient can be positioned with the long axis of his or her body extending in any desired radial direction and with any portion of his or her body at the polar axis. For example, if the patient's head is positioned at the polar axis, as where procedures or imaging are to be performed on the head, the patient's feet can point in any direction. In one arrangement, the connecting elements include a pair of connecting elements such as a pair of opposed, heavy, plate-like walls disposed at least about 14 feet apart from one another and defining two opposite ends of a room. In other embodiments, the polar axis may extend horizontally, and the pole supports may extend along walls of the room defined by the magnet frame.

In yet another aspect of the present invention, there is provided a diagnostic facility comprising a magnet, such as the magnets described above and magnetic resonance imaging apparatus utilizing the magnetic field applied by the magnet to provide an image of a patient received in the patient-receiving gap. Preferably, this facility includes one or more devices for performing or assisting in diagnostic procedures on a patient disposed in the patient-receiving gap. These devices are accessible within the working space. Preferably, the facility includes a staging area that includes a plurality of patient-carrying devices for carrying patients from the staging area to the patient-receiving gap and for supporting patients during diagnostic procedures. The patient-carrying devices may be pre-positioned and arranged within the staging area to provide for substantially continuous usage of the magnet for performing substantially continuous diagnostic procedures. Most preferably, one of the plurality of patient-carrying devices is positioned within the patient-receiving gap of the magnet, while one or more additional patient-carrying devices are outside of the patient-receiving gap. In a particularly preferred arrangement, the facility includes a plurality of preparation rooms and an infeed passageway communicating with the preparation rooms, so that patients can be positioned on the patient-carrying devices in the preparation rooms and can be carried on such devices through the infeed passageway into the patient-receiving gap of the magnet. Most preferably, the infeed passageway extends to the patient-receiving gap of the magnet from one side of the gap, and the facility includes an outfeed passageway extending from the other side of the patient-receiving gap. The outfeed passageway desirably leads back to the preparation rooms. In this arrangement, a succession of patients can be pre-positioned on the patient-carrying devices, and can be conveyed in sequence through the infeed passageway, into the magnet for imaging and then out of the magnet after imaging and back to the preparation rooms through the outfeed passageway.

A further aspect of the invention provides methods of magnetic resonance imaging wherein a succession of patients is conveyed into and out of a magnet in the manner discussed above, each patient being imaged while that patient is positioned in the patient-receiving gap of the magnet.

In yet another aspect of the present invention, there is provided a method of magnetic resonance for diagnostic purposes including the steps of positioning a patient within a gap defined by a frame of a magnet, positioning a technician within a working space within the frame of the magnet adjacent the gap, obtaining magnetic resonance data from the patient using a magnetic field applied by the magnet. Preferably, this method includes the step of having the technician in the working space assist the patient during one or more of the following phases of the procedure: positioning the patient within the gap; performance of diagnostic procedures while the patient is within the gap; and removal of the patient from the gap. The step of obtaining magnetic resonance data optionally may be performed so as to generate a magnetic resonance image of the patient.

A further aspect of the invention provides improved resistive coils for magnetic resonance imaging static field magnets. A coil according to this aspect of the invention includes a plurality of spiral windings extending around an axis. Each winding has an inner end adjacent the axis, an outer end remote from the axis and a conductor extending in multi-turn spiral between the inner end and the outer end. The windings include one or more outward windings and one or more inward windings. The turns of each outward winding are arranged such that a point moving along the turns in a first direction of rotation about the axis moves from the inner end towards the outer end. The turns of each inward winding are arranged so that a point moving along the turns in the first direction of rotation about the axis moves from the inner end towards the outer end. The windings are stacked one above the other along the axis and are electrically connected in series with one another. The electrical connections between the windings most preferably include one or more interior connections, the inner end of one of said inward windings being connected to the inner end of one of said outward windings at each such interior connection. The connections typically also include one or more exterior connections, the outer end of one of the outward windings being connected to the outer end of one of the inward windings at each such exterior connection. Most typically, the inward windings and the outward windings are arranged in alternating sequence along the axis. The interior connections and the exterior connections are also arranged in alternating sequence along said axis. As further discussed below, such a coil will provide essentially the same magnetic performance as a solenoid wound with an equal number of turns. However, the coil in accordance with this aspect of the invention can be fabricated more readily than a conventional helical coil having multiple helical layer nested within one another, particularly where the conductor is a relatively stiff element such as a metallic bar having cross-sectional dimensions of about 5 mm or more.

Preferably, the conductors of the windings are tubular so that each said winding has a bore extending through the conductor between its inner end and its outer end. The coil may further include a plurality of coolant ports communicating with the bores of the windings. The ports serve as coolant inlets and coolant outlets for passing coolant through said windings. The coolant ports desirably are arranged so that the bore of each winding is connected in a fluid flow path between a coolant inlet and a coolant outlet, but so that each fluid flow path extends through less than all of said windings. Thus, different windings are connected in different fluid flow paths. Each fluid flow path provides flow resistance far less than that which would be expected in a single flow path extending through the entire coil. This greatly facilitates coil cooling, and minimizes heat transfer to the pole and to other surrounding structures.

Further aspects of the invention include magnets for resonance imaging including a pair of coils as discussed above and a ferromagnetic frame including a pair of ferromagnetic poles projecting along a polar axis defining a patient-receiving gap therebetween, the poles having proximal ends remote from the gap and tips bounding the gap. The frame further includes a ferromagnetic flux return structure extending between poles.

Yet another aspect of the invention provides methods of fabricating a coil for a magnetic resonance imaging magnet. Methods according to this aspect of the invention desirably include the steps of a plurality of inward and outward spiral windings as discussed above, the windings being separate from one another; superposing the spiral windings one above the other so that said spiral windings are substantially coaxial with one another; and electrically connecting the windings in series with one another. The connecting step desirably includes the step of forming one or more interior connections and exterior connections as discussed above. Preferably, the conductors constituting the windings are tubular. The step of electrically connecting the windings in series with one another includes the step of joining the tubular windings to one another so as to form a continuous fluid path between windings at at least some of said connections.

Yet another aspect of the invention provides a magnet for magnetic resonance imaging having a ferromagnetic frame defining a patient-receiving space and a source of magnetic flux in magnetic circuit with said frame so that flux produced by said source will pass through said patient-receiving space and through said frame; and means for suppressing temperature changes in the frame during operation. Most preferably, such means include thermal insulation covering at least a part of said frame. This aspect of the invention incorporates the realization that changes in the magnetic properties of the frame due to changes in temperature of the frame can cause changes in magnetic fields in the patient-receiving space. By suppressing these temperature-induced changes, the magnet according to this aspect of the invention provides enhanced field stability and uniformity.

These and other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
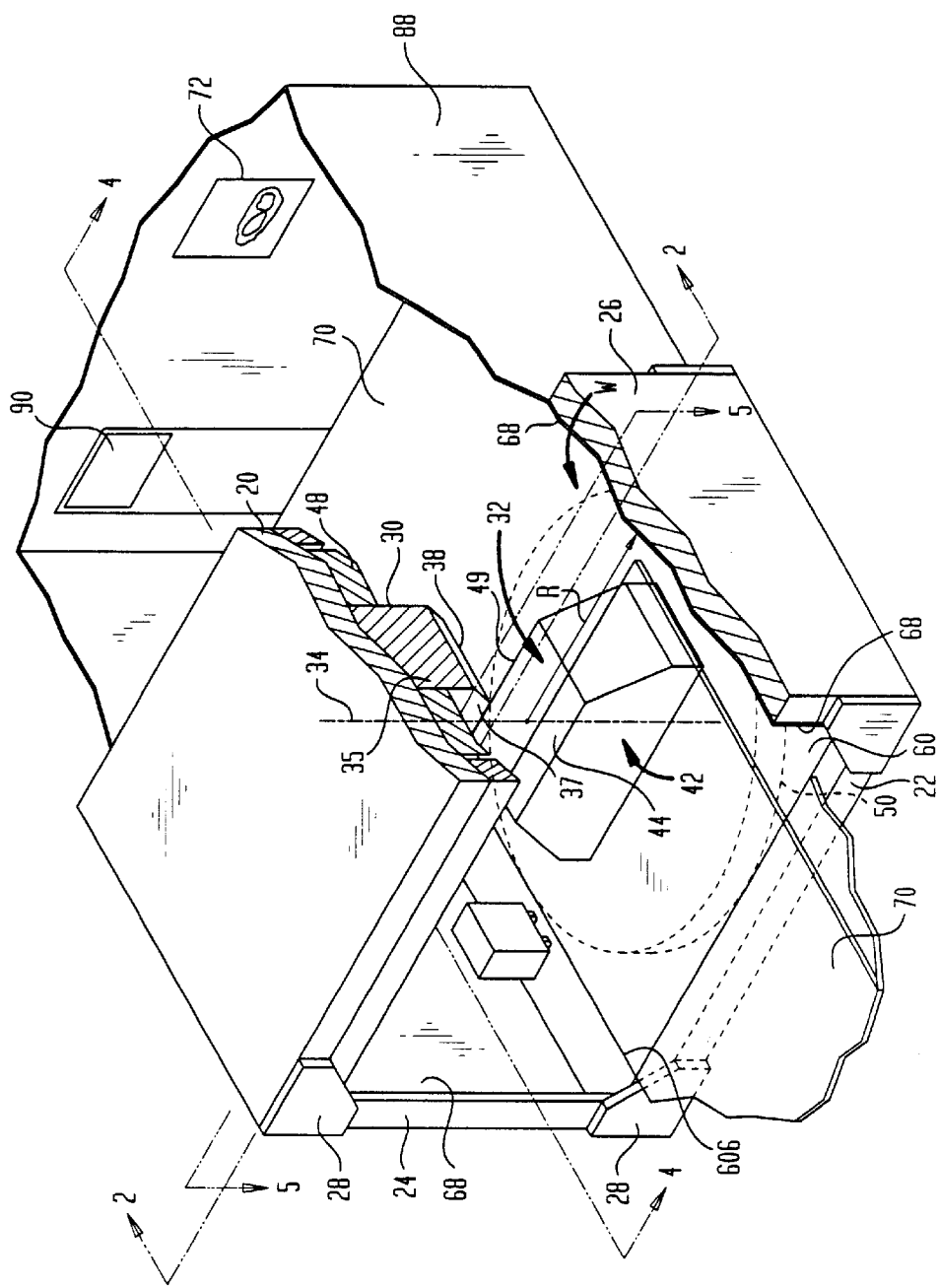
FIG. 1 is a diagrammatic perspective view depicting elements of apparatus in accordance with one embodiment of the invention.

Apparatus in accordance with one embodiment of the invention (FIG. 1) includes an upper pole support 20 and a lower pole support 22. Each of these pole supports includes a steel slab approximately sixteen feet long, ten feet wide, and about twelve inches thick. The upper pole support is held above the lower pole support by a pair of connecting elements 24 and 26. Each of the connecting elements is a steel slab approximately nine feet tall, ten feet wide, and 12 inches thick. Ferromagnetic connecting elements 24 and 26 are disposed between the pole supports at the ends thereof, so that the upper pole support lies approximately eleven feet above the lower pole support and so that the inwardly facing surfaces of the connecting elements are spaced apart from one another by a distance of approximately fourteen feet. As best appreciated with reference to FIG. 1, the pole supports 20 and 22 and the connecting elements 24 and 26 form four sides of a rectangular box. Elements 20, 22, 24 and 26 in combination provide the flux return path. Gusset plates 28 are provided at the corners of the box to reinforce it against racking and twisting stresses.

Figure 2:
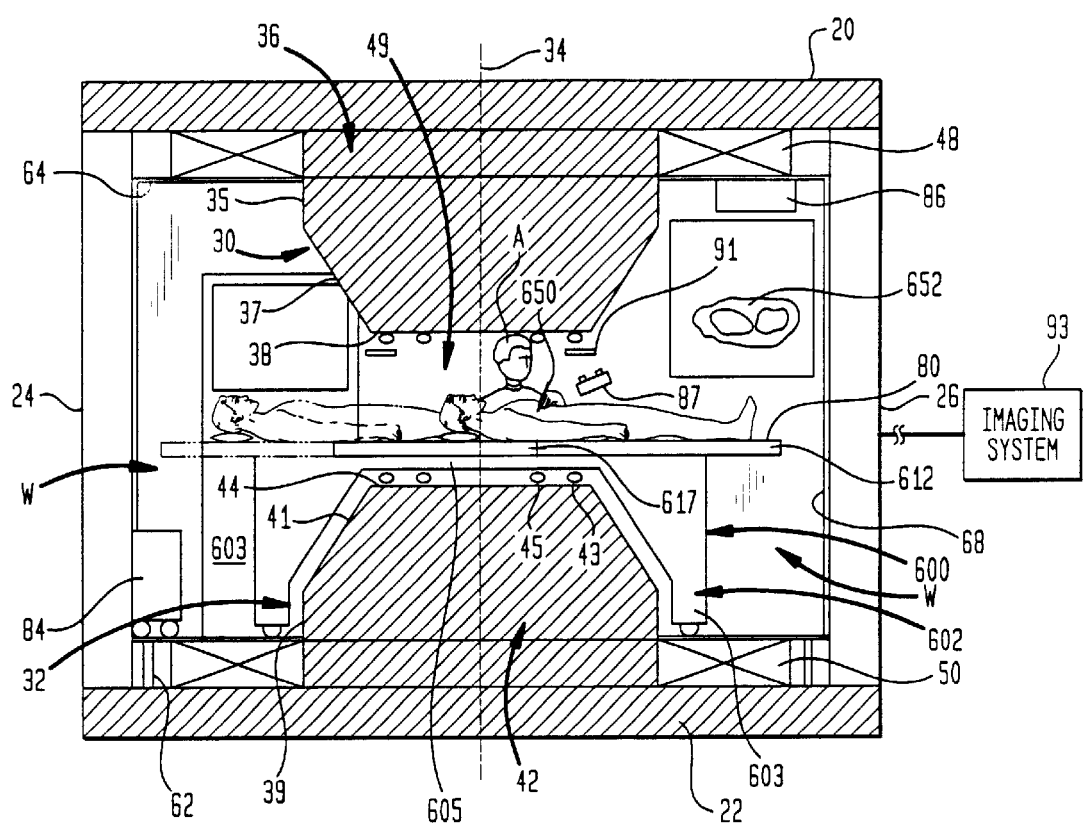
FIG. 2 is a diagrammatic sectional elevational view taken along line 2—2 in FIG. 1.

An upper ferromagnetic pole 30 projects downwardly from upper pole support 20, whereas a lower ferromagnetic pole 32 projects upwardly from the lower pole support 22. Poles 30 and 32 are generally in the form of rectangular solids. As best seen in FIG. 2, the upper pole 30 includes a ferromagnetic pole stem 36 extending from the upper pole support, a generally rectangular pole tip 38 disposed at the distal end of the pole remote from the pole support. The pole stem 36 includes a proximal portion 35 of substantially uniform cross-sectional shape adjacent the pole support, and a tapering portion 37 having a progressively smaller long dimension in the distal direction away from the pole support. The short dimension of the pole stem remains constant from the pole support to tip 38. The lower pole 32 has a similar pole stem 42, with uniform portion 39 at the proximal end of the pole and tapering portion 41 tapering inwardly in the distal direction toward the pole tip 44. The taper or progressive reduction in the long dimension of the poles minimizes saturation in the pole stem and aids in providing a uniform field even with relatively narrow poles having a small short dimension. The narrow poles provide better access to the patient for the physician or surgeon. As best seen in FIGS. 5A–5D, the proximal portion 39 of the lower pole stem has rounded corners. The proximal portion 35 of the upper pole stem has similar rounded corners. Both poles are aligned with one another and define a polar axis 34 extending vertically, transverse to pole supports 20 and 22, through the centers of the poles. The long dimensions of the poles are aligned with one another so as to provide an elongated patient-receiving gap 49 between the poles. The pole tips desirably have a ratio of long dimension to short dimension of about 4:3 or more, and more preferably about 1.5:1. For example, the pole tips may have dimensions of about 48 inches (1.22 m) by about 72 inches, whereas the pole stem bases may also be generally rectangular and may have dimensions of about 48 inches (1.22 m) by about 86 inches (2.18 m). The distance between pole tips 38 and 44 and hence the dimension of gap 49 in the axial direction along polar axis 34 desirably is at least about 17.5 inches and more desirably about 36 inches. The ratio between the shortest dimensions of the pole tips and the dimension of the gap in the axial direction is most preferably about 1.3:1. This ratio desirably is between about 1:1 and about 2:1 or less.

A resistive electromagnet coil 48 encircles the stem 36 of upper pole 30 at its juncture with the upper pole support 20. A corresponding lower resistive electromagnetic coil 50 encircles the stem 42 of the lower pole at its juncture with lower pole support 22. The electromagnetic coils 48 and 50 are also generally rectangular in shape. In this example, each one of the coils may have a width M about 33 inches and a thickness of about 12 inches. This large area keeps resistive power losses low. For superconducting coils, this area will be greatly reduced.

The apparatus also includes the other components conventionally utilized in MRI apparatus. For example gradient coils 45 (FIG. 2) are disposed adjacent gap 49 for applying magnetic field gradients. Shimming coils 43 are disposed adjacent gap 49 for providing an additional magnetic field which enhances the uniformity of the magnetic field in the gap. One or more RF transmitting and receiving antennas 91 is also provided adjacent gap 49. The components described above are linked to a conventional MRI imaging system 93 including elements such as DC power supply for energizing coils 48 and 50 and shimming coils 43; RF transmitters and receivers linked to antennas 91; and gradient coil power devices linked to gradient coils. 45. The apparatus also is provided with a conventional control computer and conventional components for transforming the received magnetic resonance signals into the desired images. Such elements are well-known in the MRI art and need not be described further herein.

The apparatus further includes raised floor 60 supported above the lower pole support 22 by braces 62. Floor 60 extends over the top of the lower coil 50. A ceiling 64 is suspended beneath upper pole support 20 by ceiling structure members 66. Wall coverings 68 may be provided on the inwardly facing surfaces of connecting elements or walls 24 and 26. Floor 60, ceiling 64 and wall coverings 68 preferably are formed from non-magnetic materials such as polymeric materials, wood fibers, paper and cementitious materials such as concrete, plaster, plasterboard and the like. The exposed, inwardly facing surfaces of the floor, walls and ceiling desirably are formed from standard architectural materials and have the appearance of ordinary room walls. Ceiling 64, wall covering 68 and floor 60 may have standard architectural features such as lamps 65 (FIG. 3) built in. As shown in FIG. 1, floor 60 may be continuous with the floor 70 of a building in which the apparatus is located. Wall covering 68 may be continuous with the walls 72 of the building. Likewise, ceiling 64 may be continuous with a ceiling (not shown) which is part of the building. Thus, the space within the magnet enclosed by floor 60, ceiling 64 and wall covering 68 constitutes part of an ordinary room. The magnet frame, including the pole supports 20 and 22 and the connecting elements 24 and 26 are disposed outside of the room. Also, the coils 48 and 50 are disposed outside of the room. In variants where the interior wall coverings 68, ceiling 64 and floor 60 are not provided, elements of the ferromagnetic frame themselves may define the interior wall surfaces of the room. For example, Where wall covering 68 is omitted, the inwardly-facing surfaces of connecting elements 24 and 26 define the interior wall surfaces of the room. In this case as well, the remainder of the connecting element lies outside of the room.

Figure 3:
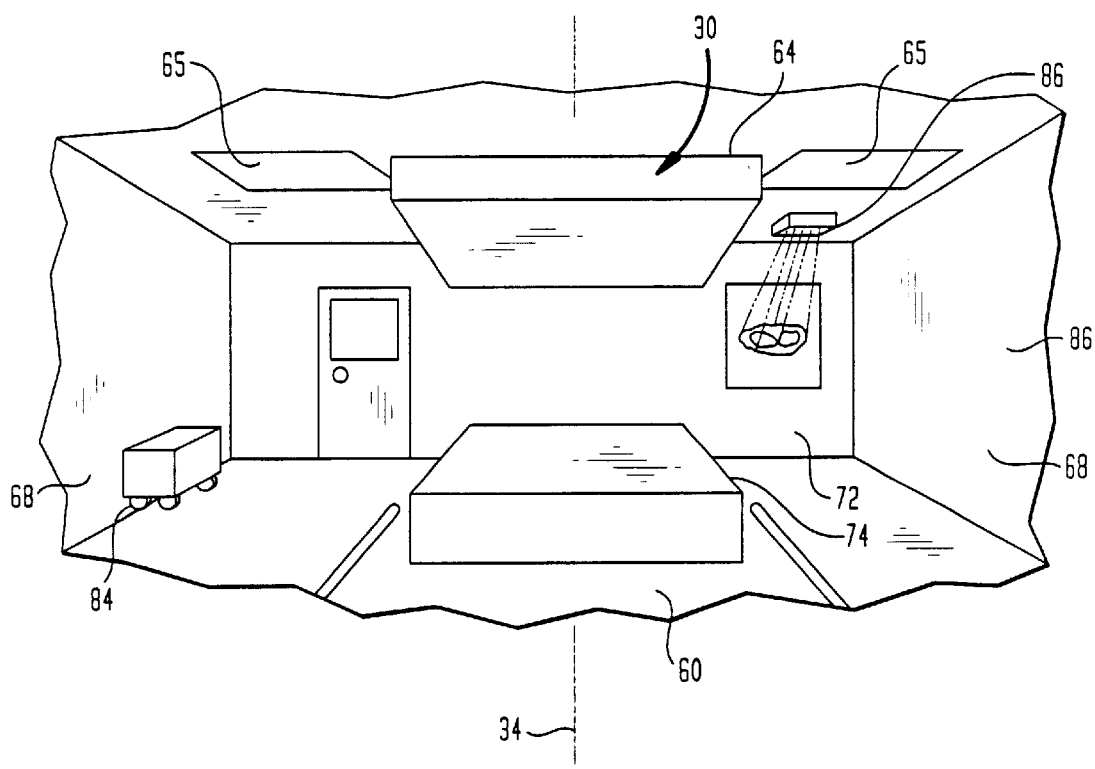
FIG. 3 is a diagrammatic perspective view taken from within the interior of the apparatus shown in FIGS. 1 and 2.

As best appreciated with reference to FIG. 3, a patient or other person inside of the room sees poles 30 and 32 protruding into the room from the ceiling and floor, but otherwise considers the room to be an ordinary room. The poles 30 and 32 desirably are concealed by shrouds 74 (FIG. 3) formed from non-magnetic materials such as polymeric materials. Thus, the apparatus is perceived by a patient as entirely open and non-claustrophobic.

As shown in FIGS. 1 and 2, the connecting elements 24 and 26 are disposed seven feet from polar axis 34. Unless otherwise specified, the distance between the polar axis and the connecting elements specified herein should be understood as referring to the smallest distance from the polar axis to any connecting element in a direction perpendicular to the polar axis, measured at the medial plane of the apparatus such as the radial distance R shown in FIGS. 1 and 2. Because the connecting elements are disposed at substantial distances from the polar axis, an adult human patient P can be positioned on a support, such as a litter or bed 80 (FIG. 2) in a generally horizontal position with his or her body extending close to the medial plane 57 and generally parallel thereto, and the patient can be disposed in any radial direction with any part of his or her body at the polar axis 34. Thus, essentially any part of a normal human patient can be imaged.

A patient positioning device 600 (FIGS. 2, 4 and 5) may be utilized with the magnetic resonance imaging system and magnet to position the patient relative to the poles and magnet gap. Device 600 desirably is formed from non-magnetic materials such as polymers. The positioning device includes a chassis 602 mounted on wheels 604. A pair of rails 606 (FIGS. 1 and 5) extend along the floor 60 of the room and also extend outwardly from the room onto the adjacent floor 70 of the building. Wheels 604 run along these rails so that chassis 602 can be moved along a first horizontal axis, denoted by arrow Z, transverse to the polar axis 34 of the magnet. This first horizontal movement direction is transverse to the long dimension of the poles. As best seen in FIG. 2, chassis 602 includes a pair of vertically-extensive end portions 603 which lie on opposite sides of the lower pole 32 when the chassis is aligned with the polar axis 34 of the magnet. A bridge position 605 of the chassis extends between the end portions, and overlies pole 32 when the chassis is aligned with the polar axis. Breaks (not shown) on wheels 604, or other devices for holding chassis 602 in position on the rails may be provided. In addition, the rails or the adjacent portions of the floor may be provided with graduations, and chassis 602 may be provided with a point or other index mark so that the chassis can be brought to a preselected disposition in the first movement or Z direction. Other positioning devices, such as a screw jack, fixed or adjustable stop or optical positioning system may be employed to locate and index the position of the chassis relative to the floor and the magnet frame.

Figure 4:
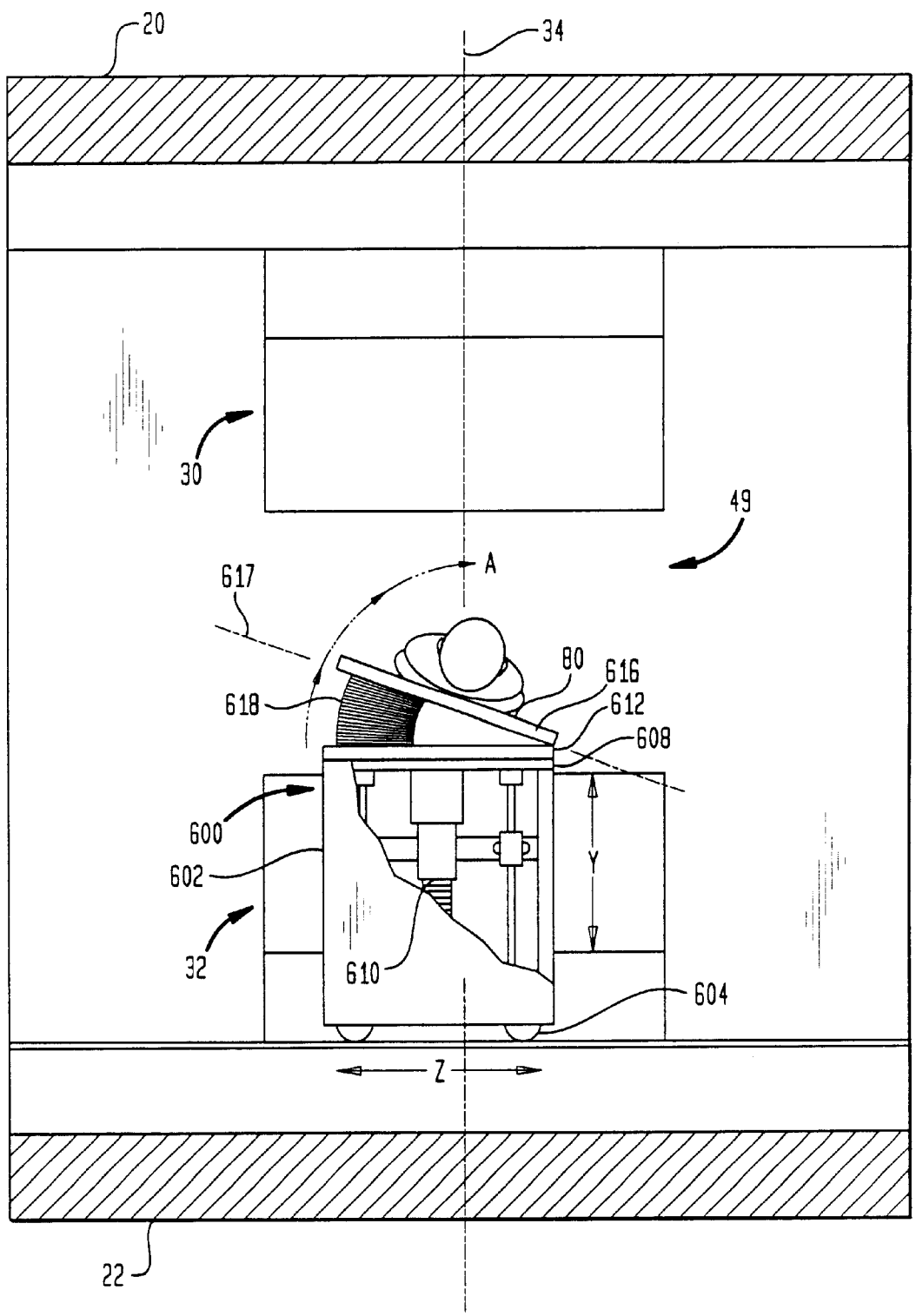
FIG. 4 is a diagrammatic sectional elevational view taken along line 4—4 in FIG. 1.
Figure 5A:
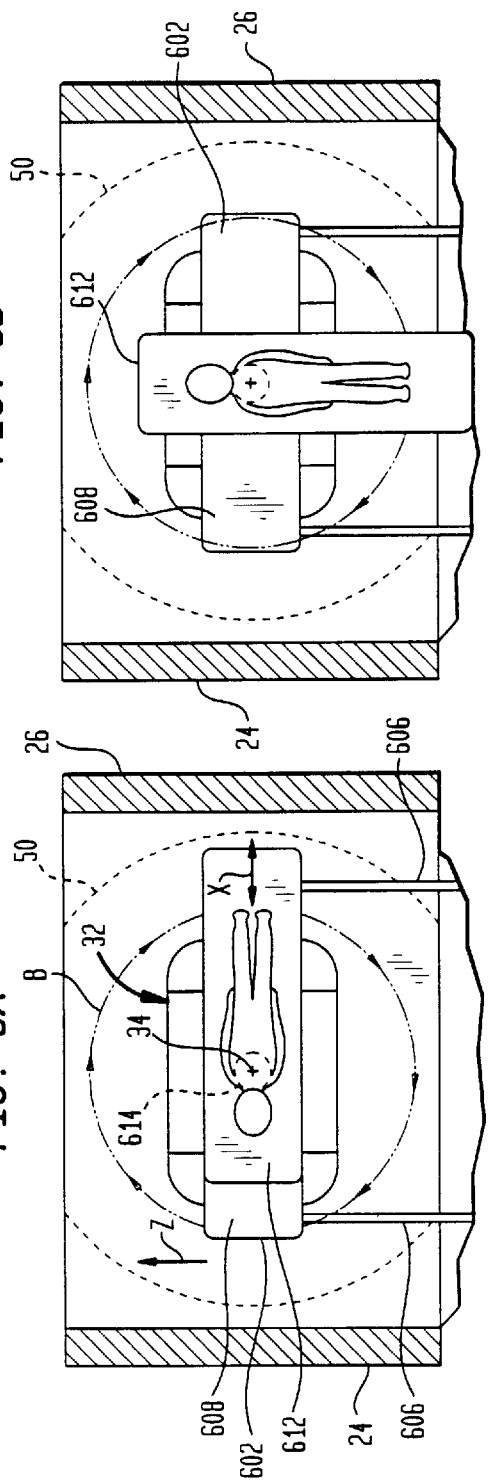
FIGS. 5A–5D are diagrammatic sectional elevational views taken along line 5—5 in FIG. 1.
Figure 5B:
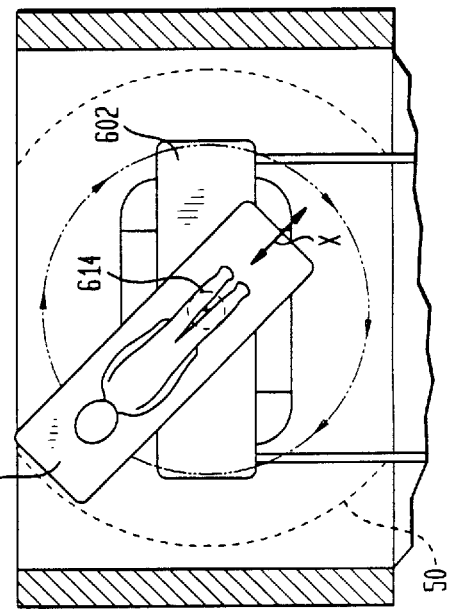
Figure 5C:
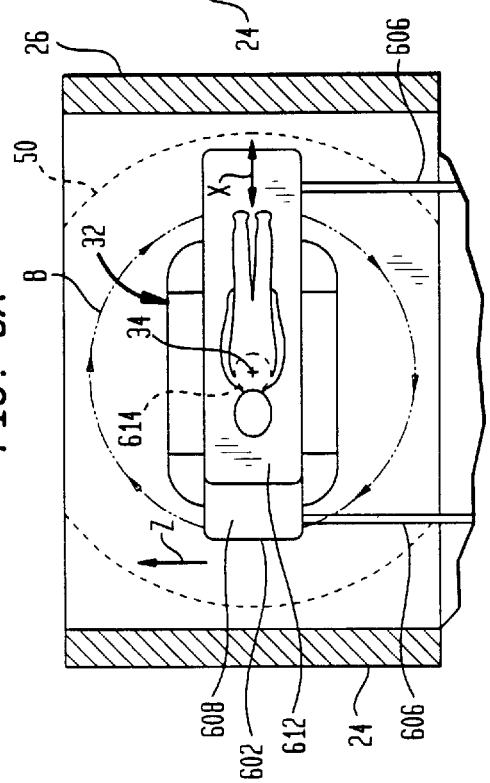
Figure 5D:
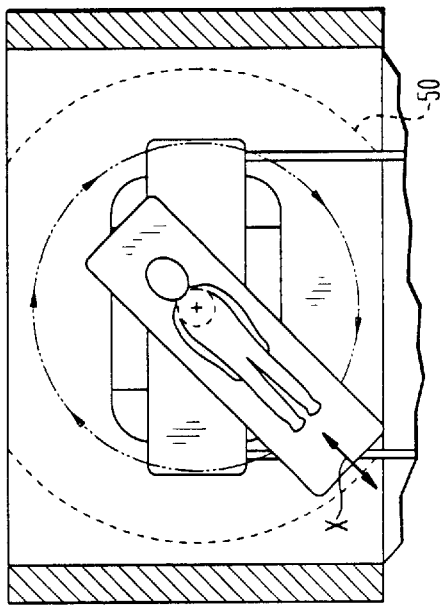

An upper member 608 is mounted on chassis 602. A screw jack 610 (FIG. 4) or other mechanical positioning system such as a hydraulic or pneumatic cylinder, lever system or the like is also provided for moving upper member 608 vertically, in the axial or Y direction, parallel to the polar axis 34 of the magnet. Positioning device 610 may be arranged to displace upper member 608 relative to the remainder of the chassis. Alternatively, upper member 608 may be fixed to the remainder of the chassis and positioning device 610 may be adapted to move the chassis 602 relative to wheels 604. An elongated, movable support 612 is mounted for pivoting movement relative to the chassis and upper member 608 around a pivot 614 (FIG. 5A). Pivot 614 is close to the center of the chassis. Thus, when the chassis is positioned in the Z direction so that the center of the chassis is coincident with the polar axis 34, the pivot 614 is also close to the polar axis. Movable support 612 is also mounted for sliding motion relative to upper member 608 and chassis 602 in a longitudinal direction X, parallel to the long direction of the support itself. Thus, as seen in FIGS. 5A through 5D, the movable support 612 can swing in pivoting motion around pivot 614 so as to orient the longitudinal direction X at any desired angle to the first movement direction Z. Thus, the longitudinal direction X of the movable support can be oriented in any direction relative to the long axis of the rectangular poles 30 and 32. By moving the movable support relative to the chassis 602 in its longitudinal direction, various locations along the length of the movable support 612 can be aligned with the polar axis 34 of the magnet.

Additionally, the litter or actual patient-carrying device 80 is mounted to the movable support 612 for pivoting movement around a tilt axis 616 parallel to the longitudinal or X direction of the movable support. Thus, as seen in FIG. 4, the tilt axis 616 extends into and out of the plane of the drawing. A tilt actuation device 618, such as a pneumatic bladder or pneumatic cylinder, screw jack, or wedge jack, is provided for tilting the litter through a range of tilt angles A. The patient support is also pivotable relative to the movable support about an inclination axis 617 transverse to the lengthwise direction of the support and transverse to the tilt axis. An inclination actuator (not shown) similar to the tilt actuator is provided for pivoting the support about the inclination axis. This allows positioning of the patient in a Trendlenburg or counter-Trendlenburg position. Thus, the patient positioner 600 provides litter or support 80 with movement in six degrees of freedom: translation in a first lateral direction Z transverse to the polar axis; translation in the X or longitudinal direction of the movable support 612, also transverse to polar axis 34 and at an arbitrary angle to the first or Z direction; rotation in a horizontal plane transverse to the polar axis so as to orient the longitudinal direction X at any angle B relative to the long axes of the poles; elevation or axial movement Y (FIG. 4) parallel to the polar axis; tilt to any desired angle A to the horizontal plane; and inclination so as to raise either end of the support. This provides extraordinary versatility in positioning of the patient relative to the magnet. For example, as seen in solid lines in FIG. 2, the head and neck of the patient is substantially aligned with the polar axis. Translation in the longitudinal direction allows positioning of the feet adjacent the polar axis, as seen in broken lines in FIG. 2. Other arbitrary positions of the patient relative to the polar axis and relative to the remainder of the magnet are also shown in FIGS. 5A through 5D. Of course, the large clearance within the magnet provided by the ferromagnetic frame discussed above also contributes to the positioning versatility. Because the connecting elements are spaced at a radial distance R from the polar axis of about seven feet or more, longitudinal movement of the patient relative to the frame can be accommodated over a range sufficient to position essentially any part of the patient's body at the polar axis.

The ability to position the patient in essentially any arbitrary location and position relative to the magnet, and relative to the vertical is extremely desirable both in imaging and in image-guided surgery. Certain surgical procedures are best performed in certain orientations of the patient. Also, the best images of the patient are acquired in the region immediately adjacent the polar axis. Therefore, the region of interest of the patient may be positioned at the polar axis to assure optimum imaging of the region of interest.

The system may include more than one patient support 600. In this case, a new patient can be positioned on the patient support and brought to the desired orientation and position at a remote location (not shown) outside of the magnet, while another patient is positioned in the magnet. After the procedure on the existing patient in the magnet is completed, the existing patient can be wheeled out of the magnet on his or her patient support 600 and the new patient support 600, with the new patient thereon, can be rolled into the magnet and positioned in the Z or first movement direction. If the Z or first direction positioning will not vary between successive patients, a fixed stop or lock may be provided, so that the new patient can be fully positioned simply by rolling the new patient support 600 along the rails until the stop or lock is encountered. The ability to position the patient without occupying the MRI system minimizes the idle time of the MRI system between patients and enhances the productivity of the MRI system.

As illustrated in FIG. 2, the physician P is performing an MRI-guided medical procedure on the patient. In this instance, the physician is advancing a surgical probe. 650 having an MRI-visible tip into the body of the patient. The imaging system and MRI magnet are operating so as to continually prepare new images of the patient. These images include an image 652 of the surgical probe 650, also showing the patient's internal structures. Thus, as the probe and the internal structures of the patient move, the displayed image including the representation 652 of the probe continues to portray the correct relative positions of the probe and internal structures. The physician therefore can use this image for guidance as he or she moves the probe and conducts the procedure. Of course, as MRI can also show different tissues within the body in contrast, the physician can use the image of the body structures for guidance in performing the treatment. For example, where a surgical operation is performed to treat a tumor, the MRI system can be operated to acquire an image which shows the tumor in contrast to surrounding normal tissue. The image contrast can be used to monitor the success of the therapy. These capabilities are particularly valuable in performing "minimally invasive" procedures, i.e., procedures which only a relatively small probe such as an endoscope or catheter is advanced into the body, percutaneously or through a small surgical opening or a natural body orifice. Of course, other medical and surgical procedures can be performed while the patient is disposed in the magnetic gap 49 and while MRI imaging is conducted. The environment within the magnet frame constitutes an operating room, and desirably includes the features normally found in operating rooms as, for example, proper lighting sanitation features, life support systems and other surgical apparatus. The essentially unimpeded access to the patient, and freedom of patient positioning provided by the magnet and patient positioning system greatly facilitate performance of these and other medical procedures while the patient is continually imaged by the MRI system. Of course, because MRI does not use ionizing radiation such as x-rays, properly conducted MRI procedures pose no appreciable health risk to the patient or to the physician. The magnetic fields impinging on the physician standing in the work space are minimal. The projecting ferromagnetic poles 30 and 32 concentrate the flux flowing from pole to pole in gap 49, between the poles. The ferromagnetic flux return path, including the pole supports 20 and 22, and the connecting elements 24 and 26 carries the vast majority of the returning flux. Moreover, the large space between the poles and the connecting elements tends to minimize flux leakage from the poles to the connecting elements. Therefore, where the physician is located is the field is minimized. To the extent that any risk is associated with exposure to such magnetic fields, the risk is diminished as compared, for example, to air-core surgical scanners. Moreover, because only a very small portion of the magnetic flux passes outside of gap 49 between the poles, movement of non-ferromagnetic metallic objects outside of the gap will not induce substantial eddy currents in such equipment. There is minimal magnetic interference with medical equipment disposed in the working space.

The space around poles 30 and 32 provides an unobstructed working space W sufficient to accommodate a physician or other adult human A (FIG. 2). This space is unobstructed by any portion of the magnet frame and extends entirely around the poles and polar axis. Thus, apart from any obstructions which may be created by the patient support 80 or the patient himself, the attendants can have access to the patient from all locations. This working space W extends to the region of the magnet between coils 48 and 50. Thus, a portion of the working space is disposed above the lower coil 50 and below the upper coil 48. The degree of access afforded by the apparatus is essentially the same as the degree of access provided in an ordinary operating room, with only a slight obstruction caused by poles 30 and 32 themselves. That obstruction is minimized by the relatively small diameter of the poles and the relatively large space between the poles.

Equipment for performing medical procedures on a patient, such as an anesthesia ventilator 84 (FIG. 2), or any other type of conventional medical equipment may be disposed inside the room, within the interior of the magnet frame. Further, a display device such as a projection unit 86 (FIG. 2) connected to the computer associated with the MRI system desirably is mounted to display an image inside the room, so that a physician or other persons performing medical procedures on a patient within the apparatus can observe the MRI image in real time, while performing such procedures. For example, one suitable projection unit is an LCD projector made by Boxlight Corporation of Paulsboro, Wash. The projection unit is a particularly desirable display because it provides a large image which can be seen by all members of the medical team in the room. One or more conventional CRT monitors and/or video goggles as discussed below can also be utilized. Control apparatus 87 such as a keyboard, joystick, mouse, or touch-sensitive elements on a monitor may also be provided inside the room, so that the attendant can control the MRI imaging process from within the room. Preferably, the working space W and gap 49 are shielded from radio frequency interference, to prevent interference with the MRI imaging procedure. Thus, the room preferably is surrounded with a continuous or substantially continuous electrically conducted shield, commonly referred to as a Faraday shield. Because the pole supports 20 and 22 and connecting elements 24 and 26 of the magnet frame are electrically conductive, these elements may serve a portion of the Faraday shield. In addition, the floor 70 and wall 72 of the building, as well as the ceiling of the room may be provided with conductive elements such as conductive mesh 88 (FIG. 1). The conductive mesh may be electrically connected to the magnet frame as by a wire or bonding strap (not shown) connecting the mesh to the frame. Doors 90 and windows 92 penetrating these walls are also provided with conductive coverings such as mesh in the doors and conductive films on windows. These conductive coverings desirably are also connected to the remainder of the faraday shield. The equipment disposed inside of the room, and hence inside of the faraday shield is designed for low RF emission. For example, the video monitor 86 may be provided with an enclosure having a conductive shield which is grounded to the frame. Also, fixtures such as overhead lights 65 may be provided with a similar shielding.

The pole supports 20 and 22, connecting elements 24 and 26, and poles 30 and 32 are arranged to provide a path with low magnetic reluctance for the flux generated, by coils 48 and 50. The flux is relatively concentrated in the poles and in regions of the upper and lower pole supports adjacent the polar axis 34. Thus, the magnetic field achievable with the magnet may be limited by magnetic saturation of the ferromagnetic material in these regions. Magnets according to the present invention typically provide fields of at least about 0.5 kilogauss, preferably at least about 1 kilogauss, more preferably at least about 3 kilogauss and desirably at least about 6 kilogauss in gap 49, but may include magnets operating at considerably higher field strengths. For example, to provide a field of about 6 kilogauss, each of coils 48 and 50 may include about 220 turns, and may be energized at a current of about 1,000 amperes to provide about 220,000 ampere-turns each. Ferromagnetic material of relatively high permeability, preferably equal to or greater than the permeability of grade 1006 steel is used in the central regions of the pole supports and in the pole stems. Preferably, the high permeability magnetic material has a permeability of at least about 50 at a field strength of 20 kilogauss or higher within the ferromagnetic material. Very high permeability materials, such as grade 1001 steel, having a permeability in excess of 50, at a field of 22 kilogauss is even more preferred.

In the regions of the pole supports remote from the polar axis and in the connecting elements, the magnetic flux spreads out over the entire width and thickness of the ferromagnetic material. Therefore, the magnetic flux is substantially less concentrated in these regions and magnetic material of lower permeability can be used if desired. Moreover, because the pole supports and connecting elements are disposed outside of the space occupied by the patient and the attendant, the size of these elements is essentially unlimited. Adding more material does not impede access to the patient. Thus, essentially any ferromagnetic material of modest magnetic conductivity can be provided in these elements without impairing access to the patient, simply by providing more ferromagnetic material. Accordingly, in these regions of the frame, the choice between using a relatively thin element at high permeability material and a thick element of lower permeability material is controlled by considerations such as economics and the weight of the resulting structure.

Coils 48 and 50 may be replaced by superconducting coils. Superconducting coils typically are enclosed in vessels referred to as cryostats filled with a coolant such as liquid helium for conventional low temperature superconductors such as NbTi or $Nb_3Sn$ or, preferably, liquid nitrogen for high temperature superconductors. The coolant maintains coils at temperatures low enough to provide superconductivity. The required temperature of course depends upon the composition of the superconducting material. Preferred promising superconducting materials such as BSCCO and YBCO provide superconductivity at temperatures up to about 77° K, the boiling point of liquid nitrogen, or at even higher temperatures (see for example Superconductive Components, Columbus, Ohio, Eurus Technologies, Inc., Tallahassee, Fla.). This minimizes the amount of energy which must be expended to cool the coils and also greatly simplifies the design of the cryostats and associated components. The superconducting coils in their cryostats surround the poles in the same positions as conductive coils 48 and 50, for example, located above the ceiling and below the floor. Thus, the working space W desirably extends above one cryostat and below the opposite cryostat. However, for very high current densities small cross-section coils may alternatively be located surrounding the poles in place of the blocking magnets discussed below with reference to FIG. 8. As described, for example, in U.S. Pat. No. 4,766,378, use of a ferromagnetic frame with projecting ferromagnetic poles in conjunction with superconductive coils is particularly advantageous. The ferromagnetic frame tends to stabilize the superconducting coil and reduce field nonuniformities caused by coil movement. The present invention thus affords a way to attain the benefits disclosed in the '378 patent while also providing essentially unlimited access to the patient. Superconducting coils can be used for low fields but are particularly useful where a very high magnetic field, above about 6 kilogauss is desired within the gap.

Figure 6:
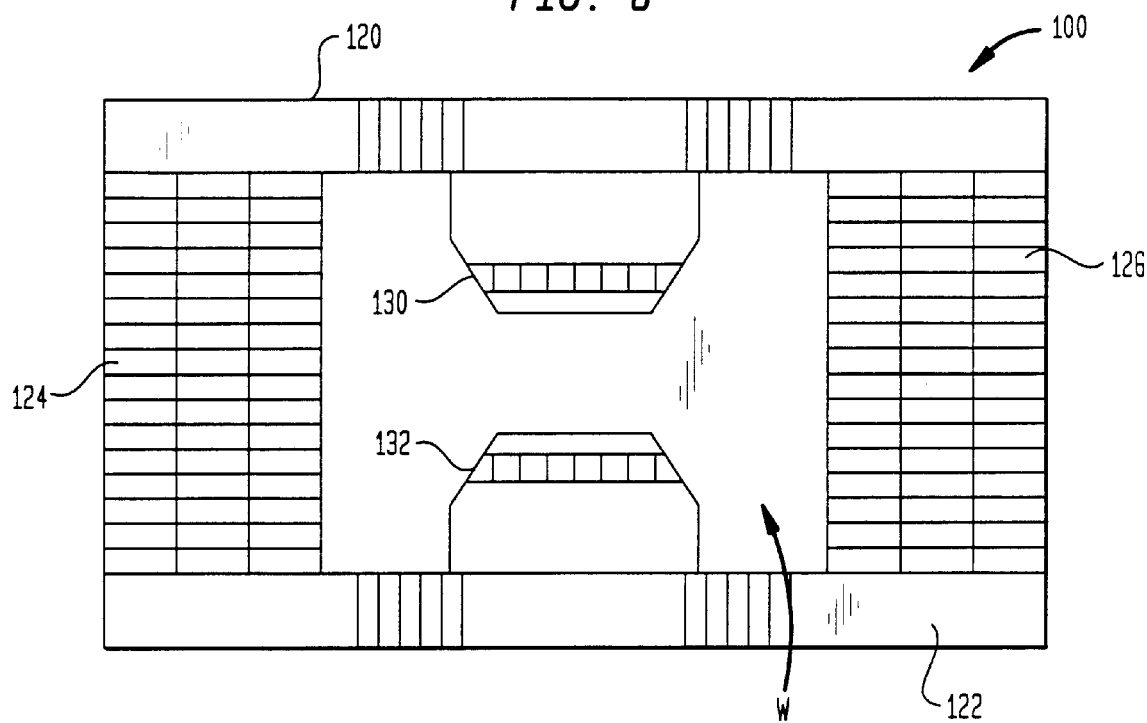
FIG. 6 is a view similar to FIG. 2 but depicting apparatus in accordance with a further embodiment of the invention.

As shown in FIG. 6, apparatus according to a further embodiment of the invention utilizes a frame 100 having permanent magnets as the source of magnetic flux. For example, the connecting elements 124 and 126 include magnetic blocks formed from a "hard"0 magnetic material, i.e., a magnetic material having high coercivity which is resistant to demagnetization. Alternatively or additionally, permanent magnets may be provided in the upper pole support 120, in the lower pole support 122, or in poles 130 and 132 themselves. Here again, because the pole supports 120 and 122 and the connecting elements 124 and 126 are disposed outside of the working space W, and outside of the space occupied by the patient, there is essentially no physical limit on the size of these elements. Therefore, these elements may incorporate essentially any amount of permanent magnet material. This facilitates the use of relatively low-energy magnet materials as an alternative to high energy product materials to provide some or all of the magnetic flux.

Figure 7:
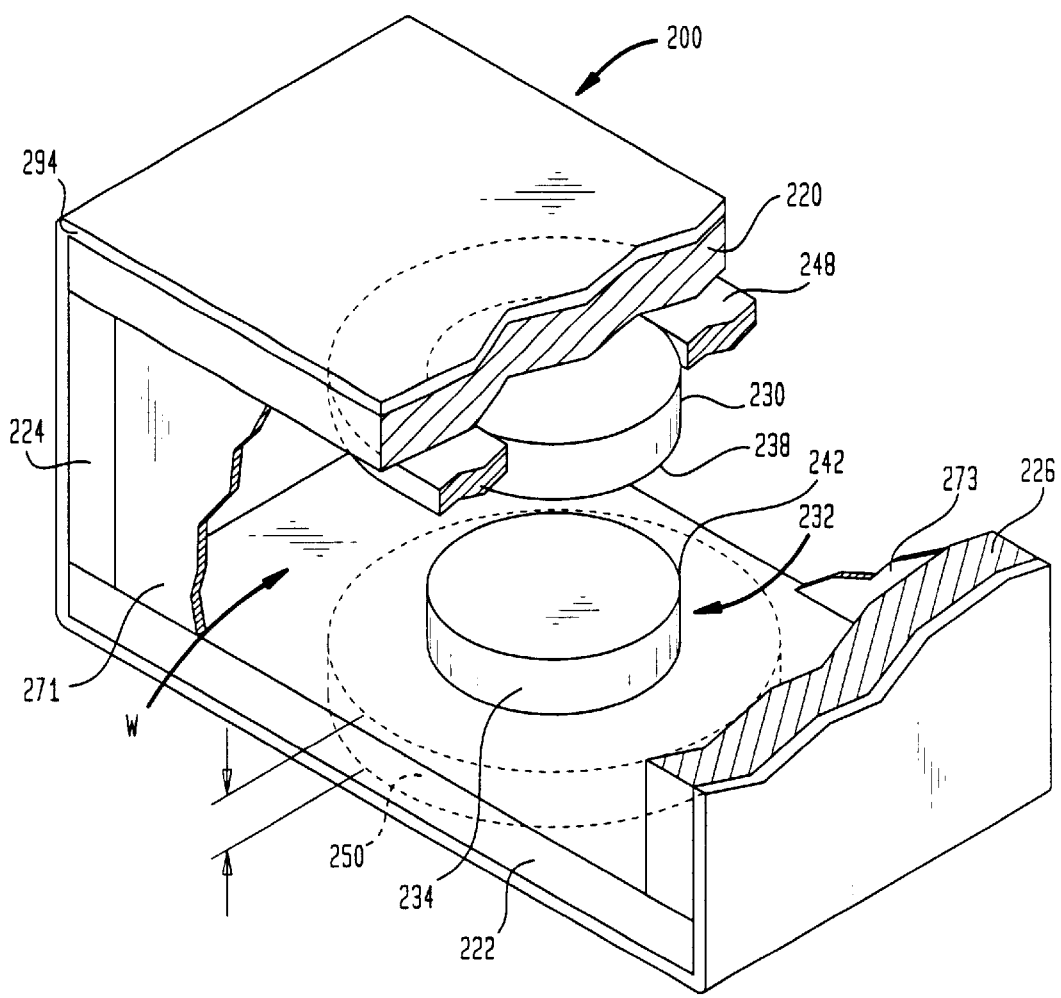
FIG. 7 is a diagrammatic perspective view depicting apparatus according to a further embodiment of the invention.

As shown in FIG. 7, apparatus in accordance with a further embodiment of the invention includes a frame 200 having pole supports 220 and 222 and connecting elements 224 and 226 similar to those discussed above. The frame includes upper and lower poles 230 and. 232, which are generally cylindrical, and about 48 inches in diameter. The distance between pole tips 238 and 244 and hence the dimension of gap 249 in the axial direction along polar axis 234 desirably is about 36 inches. Here the ratio of the shortest dimension of the pole tips transverse to the polar axis 234 (the diameters of the pole tip) to the axial dimension of the gap distance is about 1.75:1. As discussed above with reference to FIG. 1, this ratio desirably is between about 1:1 and about 2:1.

Figure 8:
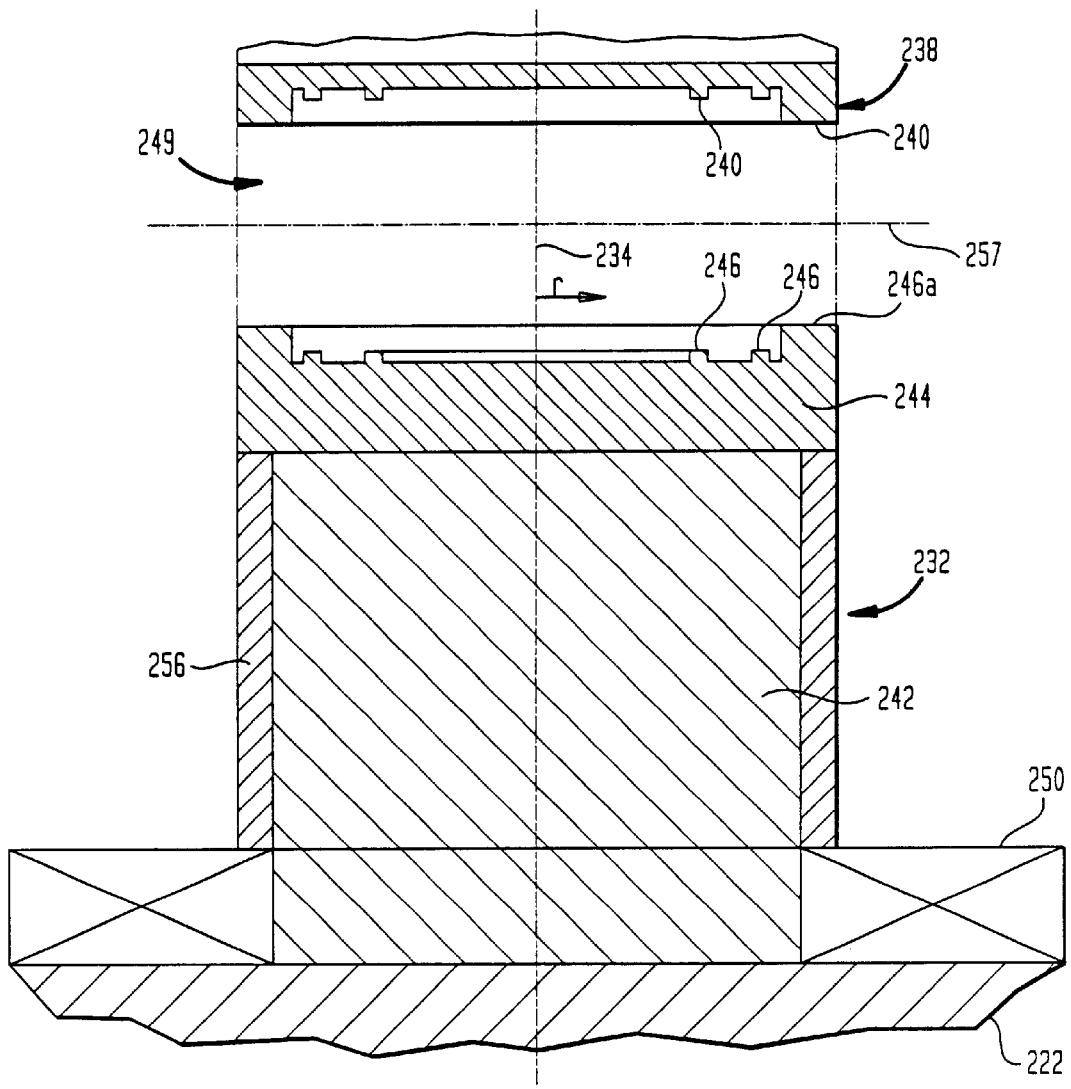
FIG. 8 is a fragmentary sectional view depicting a portion of the apparatus shown in FIG. 7.

As depicted in FIG. 8, lower pole includes a ferromagnetic stem 242 extending from the lower pole support 222 and a ferromagnetic tip element 244 at the distal end of the pole stem, remote from the pole support. Tip element 244 is provided with annular ridges 246 at various radial distances r from the polar axis 234. In the arrangement shown, one such ridge 246a is disposed at the outer edge of the pole tip. The upper pole tip 238 is provided with matching annular ridges 240. The ridges 246 and 240 effectively reduce the axial distance across gap 249. Thus, the ridges shape the pole surface to alter the reluctance at preferred geometric locations. The pattern of these different reluctances is selected to enhance the uniformity of the field in gap 249. This allows use of a smaller ratio of pole diameter to gap size than would otherwise be required to achieve the same field uniformity. Other structural elements which provide differing reluctances at different locations relative to the polar axis can be employed. For example, the pole stems or pole tips may have internal gaps filled with non-ferromagnetic material to provide increased reluctance at some locations.

Optionally, pole 232 may include a set of bucking elements 256 encircling pole stem 242 between coil 250 and pole tip element 244. The upper pole 230 may include a similar set of bucking elements (not shown). Coils 248 and 250 are energized to direct flux in a forward direction along the poles, so that the flux process in the forward direction through gap 249. Bucking elements 254 and 256 include permanent magnets arranged to direct flux in a rearward direction, opposite to the forward flux direction. For example, coils 248 and 250 may be activated to direct flux downwardly out of upper pole 230 and into lower pole 232, through gap 249, so that the forward direction is the downward direction. The bucking elements are arranged to direct flux into pole 230 and out of pole 232, in the rearward or upward direction. This arrangement tends to confine the flux from the coils within the poles and tends to minimize leakage of flux from the peripheral surfaces of the poles. This tends to promote a substantially unidirectional, uniform magnetic field within the region of the gap 249 adjacent the polar axis 234 and adjacent the medial plane 257, midway between the pole distal ends.

Here again, the working space W immediately surrounds the poles, so that a physician or other attendant can be positioned inside the working space to have access to a patient while the patient is disposed in the gap between the poles. Here again, the working space W extends above one coil and beneath the opposing coil.

The ferromagnetic frame also may includes ferromagnetic walls 271 and 273 extending between the pole supports on the long edges of the pole supports, i.e., on the edges of the pole supports which are not occupied by the connecting elements 224 and 226. Thus, the pole supports form two opposing sides of a hollow rectangular solid; the connecting elements 224 and 226 form two other opposing sides or wall elements and walls 271 and 273 form the remaining opposing sides or wall elements. Walls 271 and 273 desirably have openings (not shown) formed therein to provide access by a patient and an attendant to the interior of the frame. Walls 271 and 273 may be relatively thin metallic structures. These additional walls minimize leakage flux from the exterior of the frame. Conversely, these additional walls block the effects of varying magnetic fields outside of the frame on the field between the poles, and thus provide a more uniform, stable field. Also, walls 271 and 273 form electrically conductive elements of a Faraday shield to minimize RF interference with the MRI imaging procedure.

In a variant of the apparatus discussed above, the frame may be provided with a layer or shell of bucking flux elements 294 overlying the ferromagnetic elements of the frame on the outside of the frame. The bucking flux elements are permanent magnets arranged to direct flux along the exterior of the frame in a direction opposite to the direction of the flux induced by coils 248 and 250.

Figure 9:
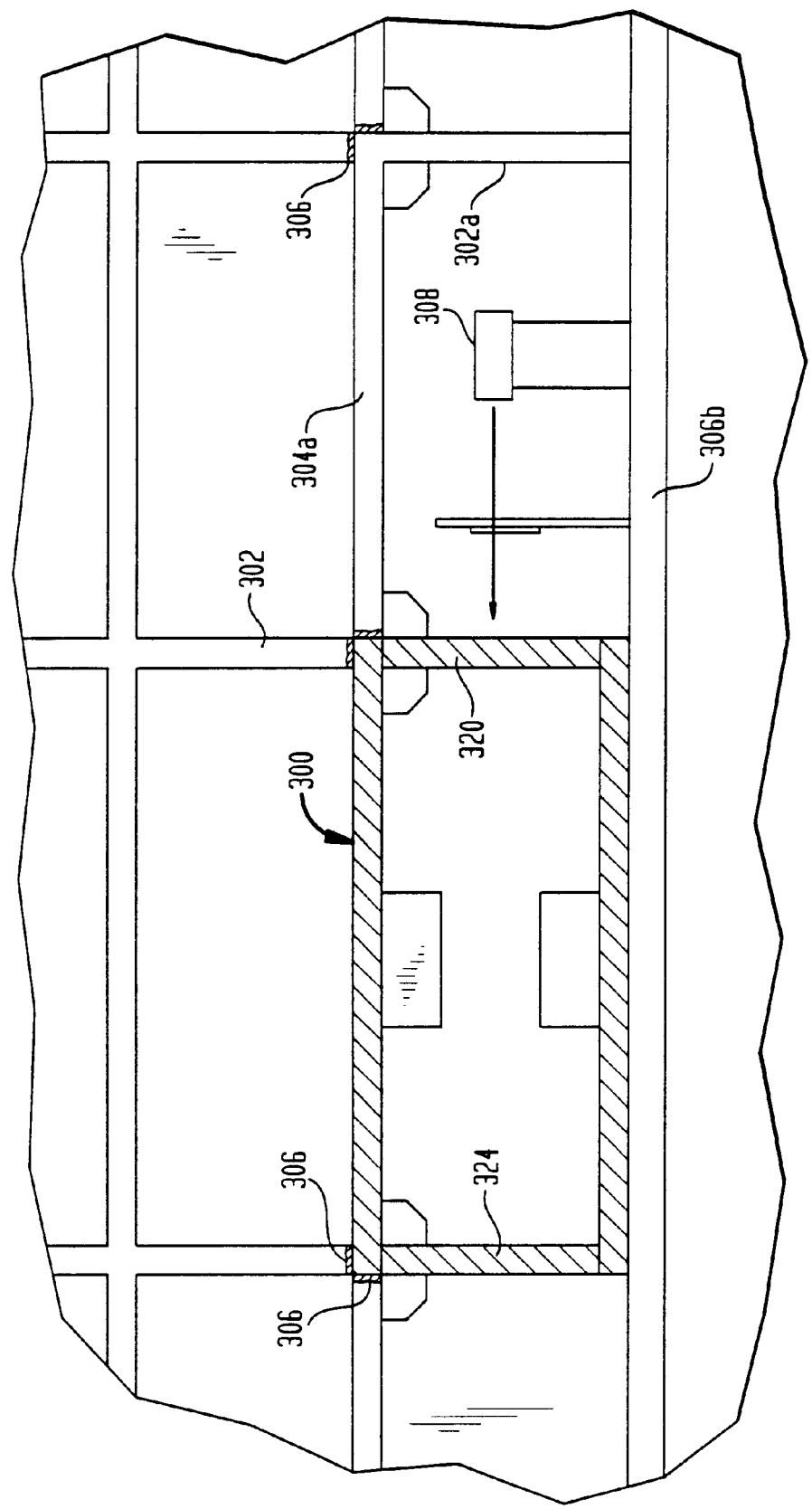
FIG. 9 is a diagrammatic elevational view depicting apparatus in accordance with a further embodiment of the invention in conjunction with a building and other apparatus.

As shown in FIG. 9, the magnet frame may be integrated with the structure of a building. For example, the connecting elements 324 and 326 of a magnet frame as discussed above may support other structural elements, such as columns 302 and beams 304. Where the beams and columns are ferromagnetic, such as in conventional steel frame construction, blocking plates 306 framed from a diamagnetic material may be interposed between the frame of the MRI magnet and the remainder of the building frame to prevent transmission of magnetic flux therebetween. This minimizes any effect of induced magnetic fields in the remainder of the building frame on the MRI imaging procedure. Alternatively, other parts of the building frame may be integrated in the magnetic circuit of the magnet frame. Thus, beam 304a, column 302a and beam 304b are connected in magnetic circuit in parallel with connecting element 326 and carry part of the magnetic flux. These elements may be isolated from other parts of the building frame by further blocking elements 306. Those elements of the building frame connected in the magnetic circuit may be protected from induced magnetic fields by appropriate shielding (not shown) or else may be located in areas of the building remote from sources of interfering magnetic field as, for example, areas remote from heavy electrical generating equipment and vehicular traffic. As also shown in FIG. 9, elements of the ferromagnetic frame may provide shielding for ionizing radiation such as x-rays or gamma rays used in therapeutic procedures. Thus, the ferromagnetic frame may be located adjacent a MRI operating room housing an x-ray or gamma ray treatment unit 308, and the treatment unit may be arranged to direct radiation towards the ferromagnetic frame. Connecting element 326 serves as a shielding wall. Alternatively or additionally, radiation-generating equipment may be disposed inside of the ferromagnetic frame, and hence inside of the room surrounded by the frame. Using these approaches, the cost of installing the ferromagnetic frame can be offset in part by cost savings achieved by eliminating other shielding structures which ordinarily would be provided in a hospital setting for the gamma ray or x-ray devices.

Figure 10:
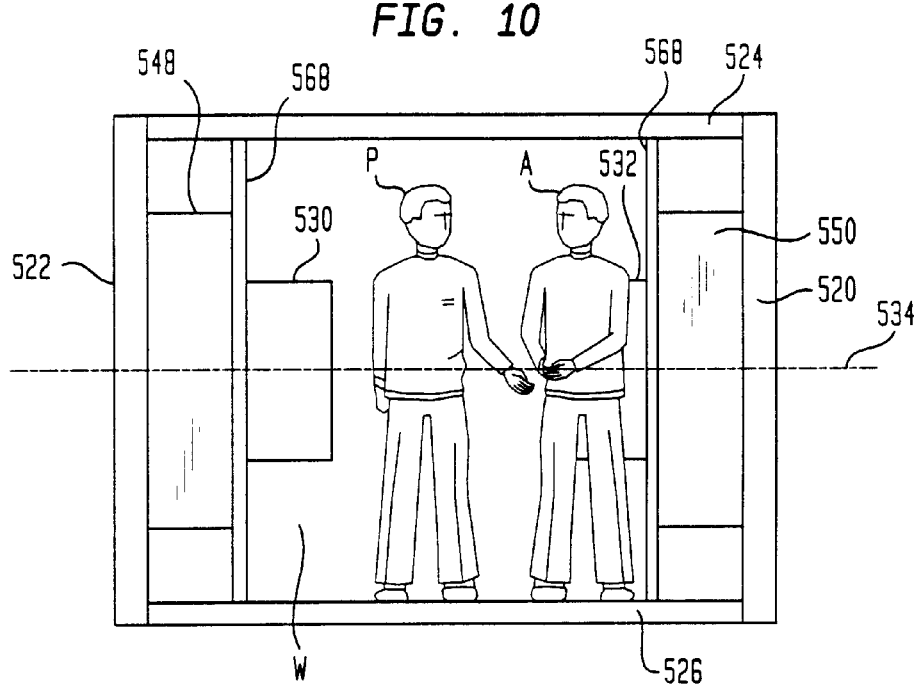
FIG. 10 is a diagrammatic elevational view depicting apparatus in accordance with a further embodiment of the invention.

As shown in FIG. 10, a magnet in accordance with a further embodiment of the invention has a polar axis 534 oriented generally horizontally, and has vertically oriented pole supports 520 and 522. Poles 530 and 532 project horizontally inwardly from the pole supports. The connecting elements 524 and 526 extend substantially horizontally. In the arrangement illustrated, coils 548 and 550 encircle the poles and are disposed in generally vertical planes adjacent the pole supports. Here again, the apparatus defines a working space W sufficient to accommodate a normal human attendant A. Once again, concealment structures such as false walls 568 may be disposed inside of the magnet frame to conceal the magnet frame from a patient. The patient has the visual impression of entering a room where the poles 530 and 532 protrude from opposing walls of the room, rather than from the floor and ceiling. Alternatively the coils 548 and 550, and walls 568 can be moved closer to the pole tips in this configuration. Apparatus with horizontally-projecting poles can be used, for example, to image a patient P while the patient remains in a generally vertical orientation as, for example, in a standing position or a position close to the standing position. The same apparatus can also be used to form an image of the patient while the patient is in a seated or reclining posture, or in essentially any other position desired. This offers considerable benefits in diagnosing and treating conditions which vary with the patient's posture as, for example, certain orthopedic conditions. Here again, the large space within the magnet frame allows the attendant to have free access to the patient while the patient is being imaged.

Figure 11:
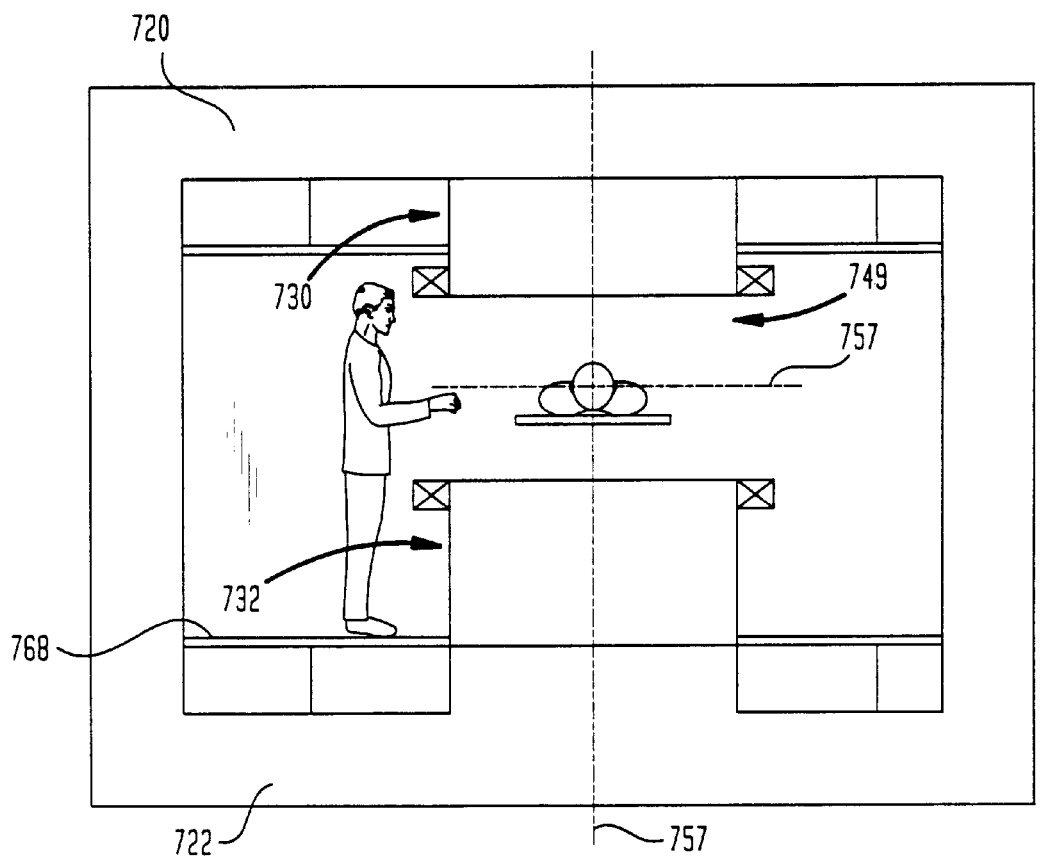
FIG. 11 is a diagrammatic sectional view depicting apparatus in accordance with yet another embodiment of the invention.
Figure 12:
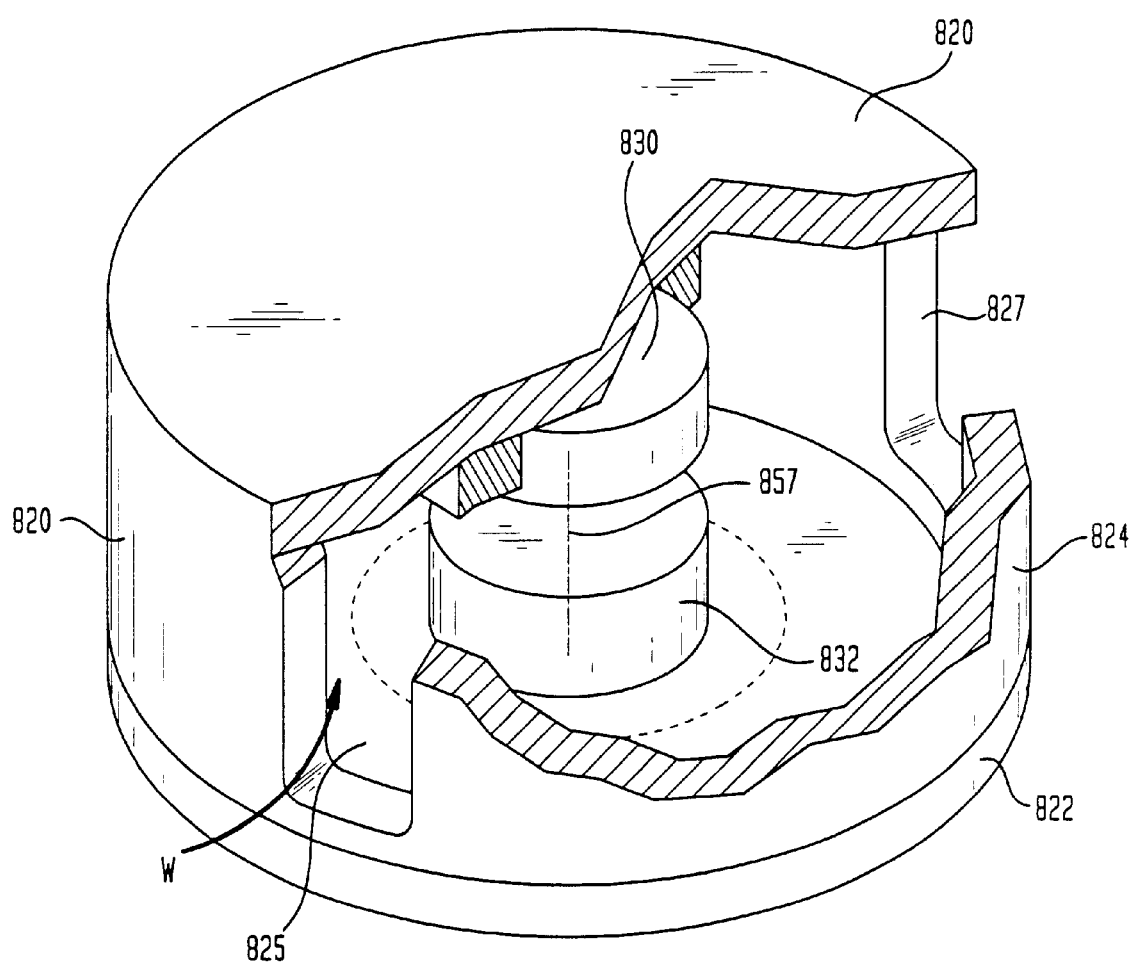
FIG. 12 is a diagrammatic perspective view depicting apparatus in accordance with a further embodiment of the invention.

As shown in FIG. 11, a magnet in accordance with a further embodiment of the invention has poles of different lengths in the axis direction. Thus, the upper pole 730 is shorter than the lower pole 732 in the axial direction, along the polar axis 757. Therefore, the medial plane 757 of the gap 749 is closer to the upper pole support 720 than to the lower pole support 722. The opposite arrangement, wherein the lower pole is shorter and the medial plane is closer to the lower pole support can also be used. Thus, by selection of appropriate pole lengths, the medial plane of the gap can be disposed at any desired elevation to facilitate positioning of the patient at a convenient height for the physician while still maintaining the area of interest of the patient in the region adjacent the medial plane of the gap, where image quality is optimized. In magnets using unequal-length poles, additional flux-shaping devices such as auxiliary coils 755, auxiliary magnets and/or shaped pole tips preferably are provided to maintain flux uniformity. In an extreme case, one of the projecting poles may be eliminated entirely, so that the gap is defined between the tip of a single projecting pole and a polar region on the face of the opposite pole support. Thus, the plate constituting the pole support serves as the pole as well. In such an arrangement, the flux-generating winding may extend around the polar region and on the surface of the pole support plate. The asymmetry of this extreme arrangement typically requires use of features such as compensating shapes on the pole tip and/or on the polar region itself, and auxiliary shim coils. The principal energizing coils of the magnet may also be asymmetric to provide additional compensation.

A magnet in accordance with yet another embodiment of the invention incorporates a generally cylindrical ferromagnetic frame. Thus, the connecting elements 824 and 826 are generally in the form of sectors of a cylinder or other body of revolution coaxial with the polar axis 857. A pair of openings 825 and 827 are provided on opposite sides of the polar axis for ingress and egress of patients and medical personnel. The upper and lower pole supports 820 and 822 are in the form of circular plates. In this particular embodiment, the poles 830 and 832 are cylindrical. However, elongated, non-circular poles, such as the rectangular poles discussed above can be employed in this embodiment as well. The working space W within the frame is in the form of an annulus encircling the poles and concentric with the polar axis.

Figure 13:
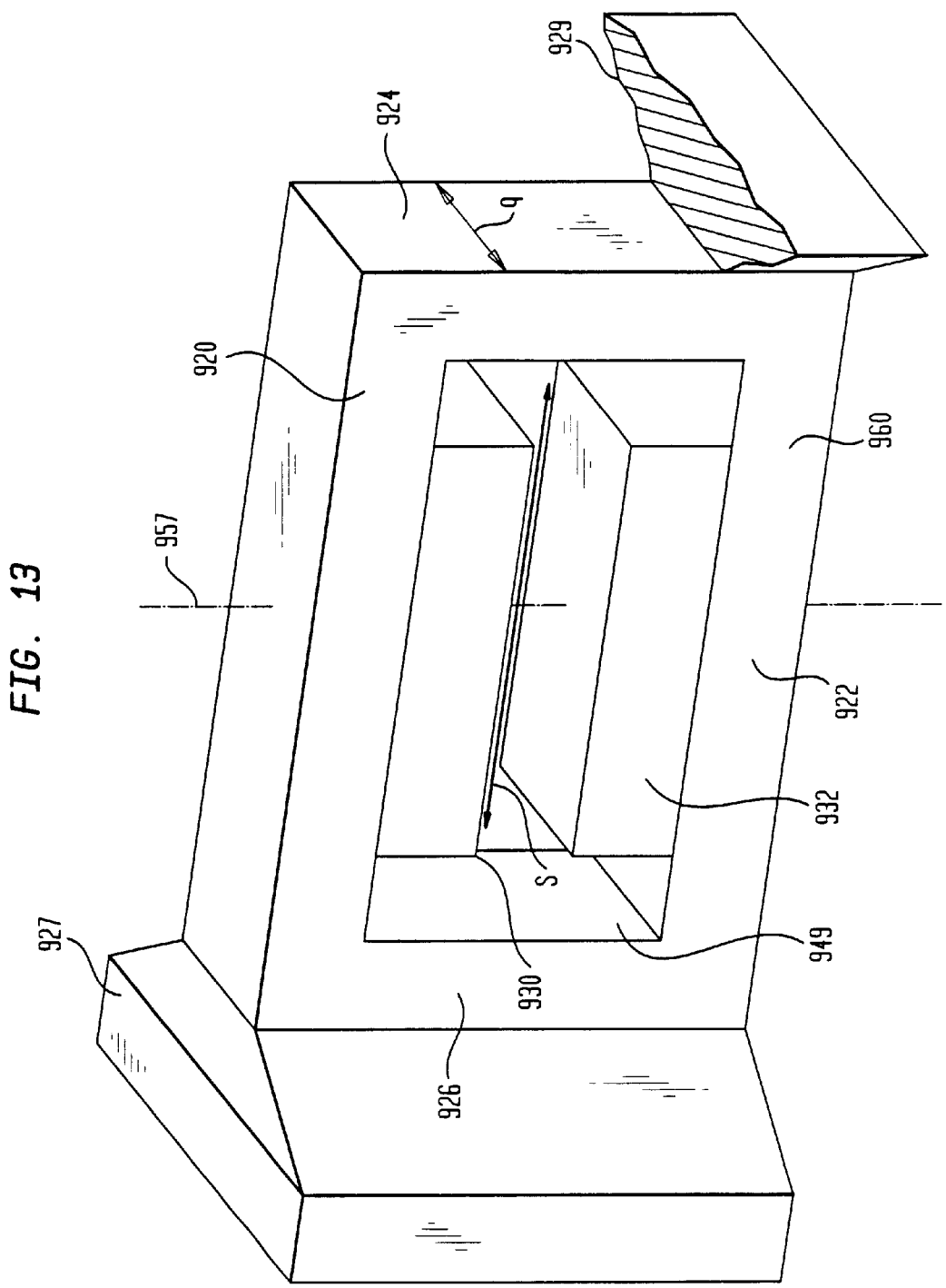
FIG. 13 is a diagrammatic perspective view depicting apparatus in accordance with a still further embodiment of the invention.

A magnet as shown in FIG. 13 has a generally flat frame. That is, the widthwise dimensions q of connecting elements 924 and 926 are not substantially larger than the corresponding widthwise dimensions of poles 930 and 932. Preferably, the widthwise dimensions q of the connecting elements in this embodiment are about 48 inches or less at least in those regions of the connecting elements closest to the gap 949. The regions of connecting elements 924 and 926 remote from gap 949 can be of essentially any dimensions. Thus, as depicted in FIG. 13, connecting element 926 includes an outwardly flowing portion 927 remote from the gap and connecting element 924 includes a similar broad portion 929 also remote from the gap. These broad portions are optional.

Desirably, the distance S between the interior surfaces of connecting elements 924 and 926 along a lengthwise dimension transverse to the polar axis and transverse to the widthwise dimensions is at least about 7 feet and most preferably between about 7 feet and about 14 feet. Poles 930 and 932 are elongated. The long dimensions of the poles extend in the direction from one connecting plane 924 to the opposite connecting element 926. In this arrangement, the frame may not define a working space inside the frame itself sufficient to accommodate a physician or other person. For example, the edges of pole 932 may lie close to the interior surfaces of the connecting elements 924 and 926 that a person cannot enter between the pole and the connecting elements. However, because those portions of the connecting elements lying close to the gap have a relatively short widthwise dimension q, a person standing outside of the frame, but alongside the frame next to the pole, can still have reasonable access to the patient disposed in gap 949. As in the embodiments discussed above, the elongated poles provide an elongated region of uniform magnetic field for imaging. The flux source is not depicted in FIG. 13. The flux source may be disposed at any location where it does not impede access. For example, the flux source may include permanent magnets incorporated into the frame. Alternatively, coils may extend around the connecting elements or the poles. If the coils extend around the connecting elements, then the distance S between the connecting elements desirably is increased to compensate for the space occupied by the coil, so that the clear span between the interior faces of the coils is at least about 7 feet and desirably between 7 feet and 14 feet.

Figure 14:
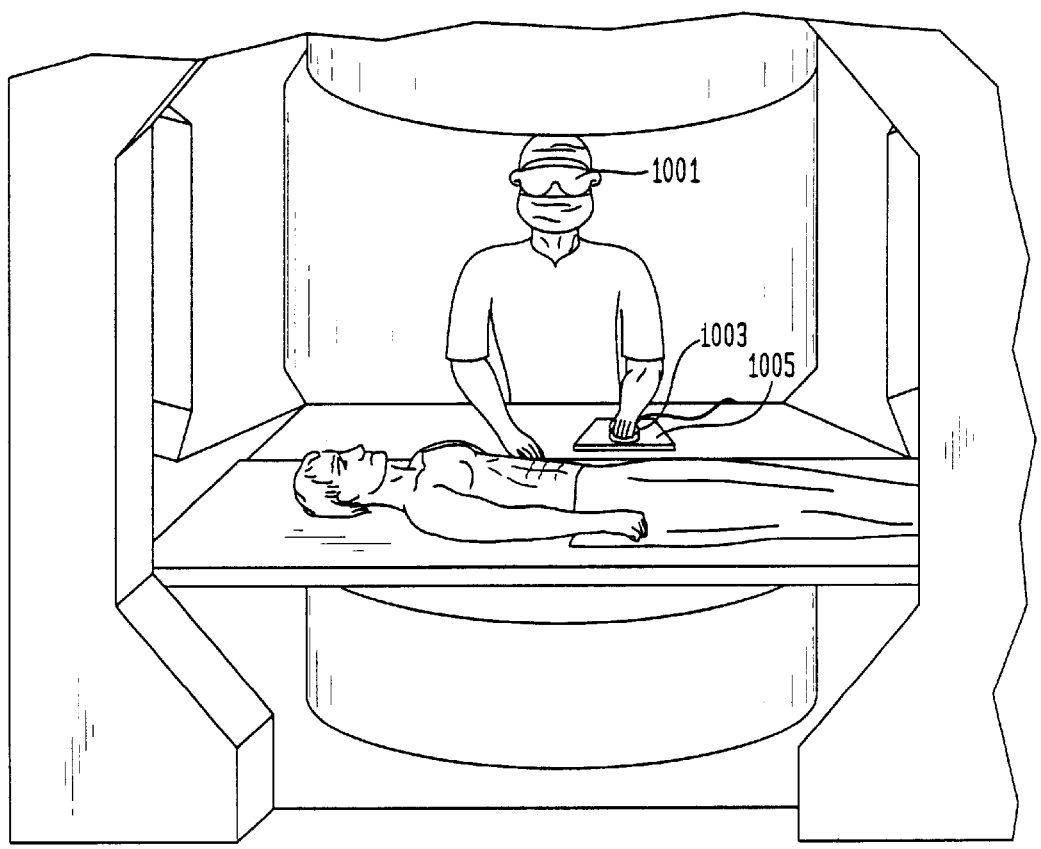
FIG. 14 is a diagrammatic perspective view depicting apparatus in accordance with another embodiment of the invention.

As depicted in FIG. 14, a further embodiment of the invention utilizes video display goggles 1001 connected to the magnetic resonance imaging unit to provide a visible display of the MRI image to the physician. The video display goggles may be arranged to display the image in front of the physician's eyes upon command. At other times, the video display goggles provide a clear vision so that the physician can see the patient in the normal manner. Alternatively, the video display goggles may be arranged to provide the MRI image superposed on the normal field of view so that the physician can observe both the MRI image and the patient simultaneously. Such superposition can be achieved, for example, using the superposition methods commonly employed in "heads up display" technology. Alternatively, the video goggles may be adapted to provide the MRI image in a corner of the visual field, so that the physician can see the image by turning his or her eyes in a particular direction as, for example, by rolling his or her eyes, away from the patient.

As also seen in FIG. 14, a mouse 1003 and a mouse pad 1005 are employed. Thus, the user interface of the MRI imaging system may incorporate a graphical user interface, wherein the user positions a cursor over a box or button appearing in the visual display and then actuates a button on the mouse to instruct the system to perform a particular action. The graphical user interface display may be shown in the same video goggles 1001 as used to display the MRI image. The mouse and graphical user interface may also be employed with a video display, such as with a projection display as discussed above with reference to FIGS. 1–3. The same mouse may be used to control a surgical robot including a surgical probe, needle or catheter. Also, both the option of the mouse control and the display options such as video goggles and projection are usable with other magnet frames, apart from those discussed above.

Figure 15:
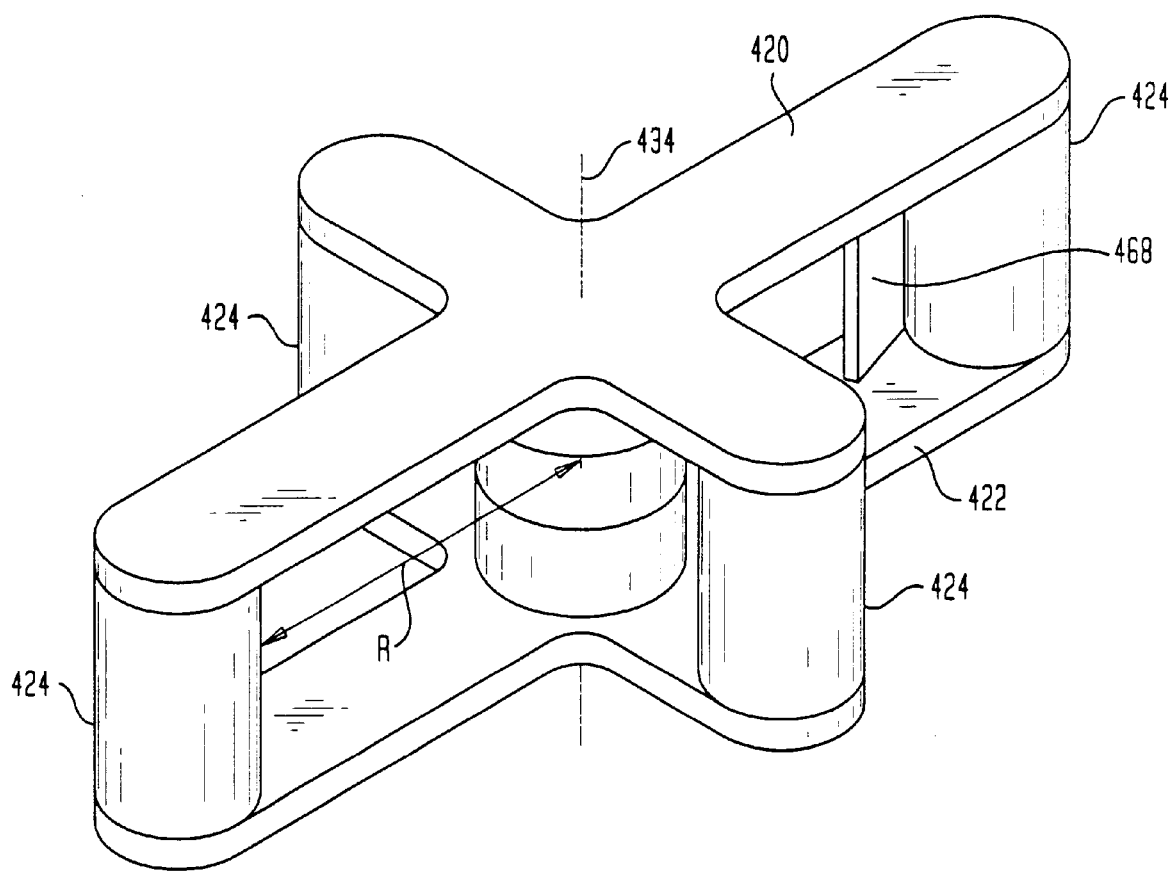
FIG. 15 is a diagrammatic perspective view depicting apparatus in accordance with another embodiment of the invention.

The configuration of the magnet frame can be varied considerably from those discussed above. For example, the pole supports 424 utilized in the frame of FIG. 15 are columns spaced widely apart from one another, rather than rectangular plates. Also, the pole supports 420 and 422 are generally star-shaped or x-shaped, and include individual legs extending away from the polar axis 434 towards each of the pole supports. Here again, the pole supports desirably are spaced at a distance R from the polar axis sufficient to provide a substantial working space around the poles. Here again, concealment elements such as a wall 468, floor (not shown) and ceiling (not shown) may be exposed inside of the region encompassed by the pole supports and connecting elements so as to define a room to conceal the frame from the patient. The overall impression again may be the impression of a normal room as discussed above with reference to FIG. 3.

A magnet according to further embodiment of the invention includes upper and lower ferromagnetic pole supports 1120 and 1122 and connecting elements 1124 and 1126, similar to the corresponding structures discussed above with reference to FIGS. 1–6. Upper and lower cylindrical ferromagnetic poles 1130 and 1132 project from the upper and lower pole supports. These poles have tips 1134 and 1136 cooperatively defining a patient-receiving gap 1138. The cylindrical poles may begenerally similar to the cylindrical poles discussed above with reference to FIG. 7. A resistive coil 1140 in the form of an elongated solenoid encircles the lower pole 1130. Solenoid 1140 has a support end 1142 disposed adjacent to the lower pole support 1130, and a tip end 1144 disposed adjacent to the tip 1136 of the pole. Upper pole 1130 is provided with an identical coil in the form of an elongated solenoid 1146. The coils desirably are encased in shrouds (not shown) so that the patient does not see the windings.

Placement of the coils so that each coil extends close to the tip of the pole enhances the uniformity of the magnetic field provided by the magnet in the patient-receiving gap 1138. To maximize this effect, the axial distance DA from the tip end of each coil to the surface of the pole tip bounding the patient-receiving gap desirably is about 6 inches or less, and most typically about 4 to 6 inches. Stated another way, DA desirably is less than about 0.25 times, and most typically about 0.1 to 0.25 times the, the gap distance or axial spacing between the poles. Lesser values of DA may be used. In this regard, it should be understood that the poles may include ferromagnetic pole caps formed separately from the remainder of the pole structure, and that such pole caps are considered parts of the poles for purposes of the foregoing dimensions. For example, where the axial length L of pole 1130 is 39 inches, and where the gap distance is about 26 inches, each solenoid may extend to within about 3 inches of the pole tip. Spacing between the support end of the solenoid and the pole supports is not critical. As explained below, it is desirable to provide for a maximum number of turns in the smallest possible radial thickness TR, consistent with other considerations. Therefore, it is desirable to place the support ends of the solenoids as close as practicable to the pole supports.

Because the coils extend around the pole, the working space W lies outside of the coils. Stated another way, a physician or technician in the working space must reach across the radial thickness TR of the coil to gain access to the working space, Therefore, it is desirable to maintain the radial thickness of the coils as small as possible consistent with other requirements. Desirably, the radial thickness of the coil is about 8 inches or less, and more desirably about 6 inches or less. The outside diameter of the coil desirably is about 70 inches or less, and more desirably about 65 inches or less, so that a physician or technician positioned in the working space can reach into the gap to the central axis of the gap without undue strain.

Figure 16:
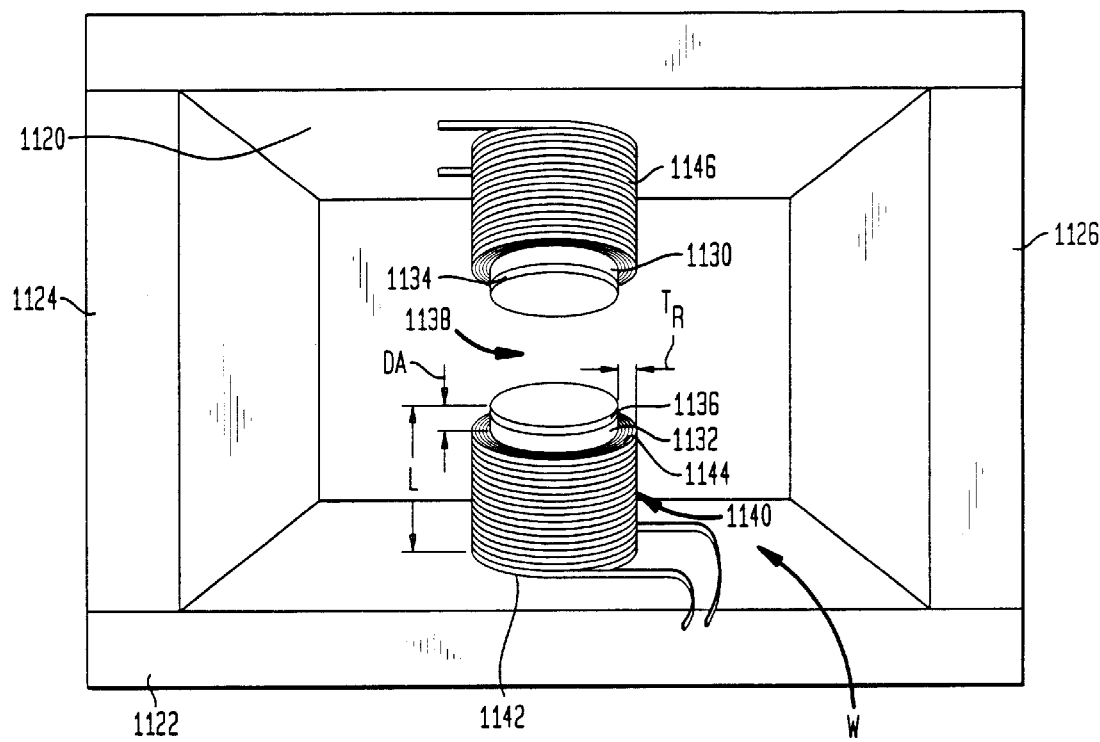
FIG. 16 is a diagrammatic perspective view of a pole and helical coil used in a magnet in accordance with another embodiment of the present invention.

In particular examples of the magnet depicted in FIG. 16, each of the upper and lower poles, 1130 and 1132, has a diameter of about 52 inches. Each of the coils 1140 and 1146 is wound in several concentric helical layers from a tubular metallic conductor of generally rectangular cross-section having a height or dimension in the axial direction of the coil of about ⅝ inch, and a width or dimension in the radial direction of the coil of about ⅞ inch. Each coil is about 36 inches long and includes between 140 and 290 turns. Thus, a coil including four concentric layers has about 144 turns and a radial thickness of about 3 inches; whereas a coil including six concentric layers has about 216 turns and a radial thickness of about 4 inches and a coil with eight concentric layers thick has about 288 turns and a radial thickness of about 5 inches. The interior bore of the tubular conductor serves as a conduit for a cooling fluid such as water, which is pumped through the bore to dissipate the heat generated by electrical resistance during operation. The coil typically carries a current of about 600 amperes to provide a magnetic field strength of about 6 kilogauss in the magnet gap.

Figure 17A:
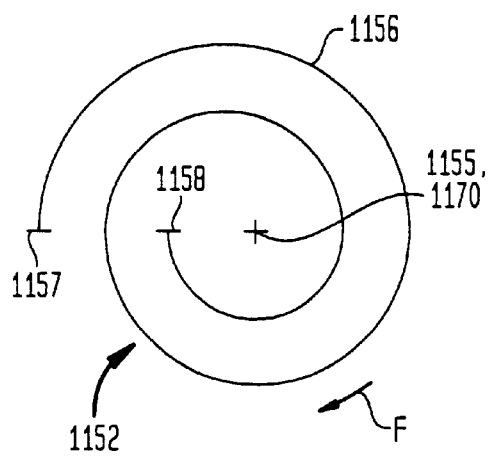
FIGS. 17A and 17B are diagrammatic views of windings incorporated in a coil according to a further embodiment of the invention.
Figure 17B:
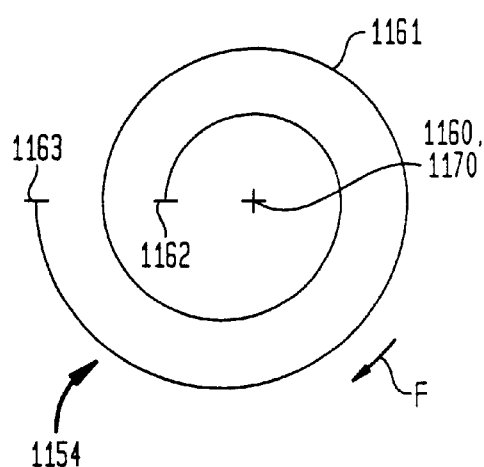

A coil according to a further embodiment of the invention includes a set of windings incorporating inward spiral windings 1152 (FIG. 17A) and outward spiral windings 1154 (FIG. 17B). Each inward winding 1152 has an axis 1155 and a conductor 1156 arranged in a multi-turn spiral. The winding has an outer end 1157 remote from the axis 1155 and an inner end 1158 adjacent axis 1155. The turns of winding 1152 are arranged so that a point moving along the turns of winding 1152 in a first direction of rotation F (clockwise as seen in FIG. 17A) about axis 1155 moves from the outer end 1157 towards the inner end 1158. Each outward spiral 1154 likewise has a conductor 1161 wound as a multi-turn spiral having an inner end 1162 adjacent axis 1160 and an outer end 1163 remote from the axis. The spiral of the outward winding is wound in the opposite sense from the spiral of the inward winding. Thus, a point moving along outward winding 1154 in the first rotational direction F (clockwise as seen in FIG. 17B) around axis 1160 moves from inner end 1162 to outer end 1163. The turns of each winding lie generally in a plane transverse to the axis of such winding. The conductors 1156 and 1161 of the various windings are formed from tubular metallic bus bars similar to the conductor discussed above. For example, the conductor may be a rectangular copper bar having a width in the radial direction of about ⅝ inch and having a height or axial dimension of about ⅞ inches, and having an internal bore of circular shape. The conductor of each inward winding 1152 defines a bore 1159 whereas the conductor of each outward winding 1154 defines a bore 1167. Only 2 full turns are shown in each winding in each of FIGS. 17A and 17B. In actual practice, the windings desirably have more than two turns as, for example, eight turns each. Also, the windings need not have integral numbers of turns. The conductors forming the turns desirably are covered with insulation such as a dielectric tape wrapped around the conductor. Although the turns are shown spaced from one another in FIGS. 17A and 17B, in actual practice the turns of each winding desirably are wound tightly against one another. The inner radius or distance from the axis to the inner end of each spiral may be about 28 inches, whereas the outer radius may about 34 inches.

Figure 17C:
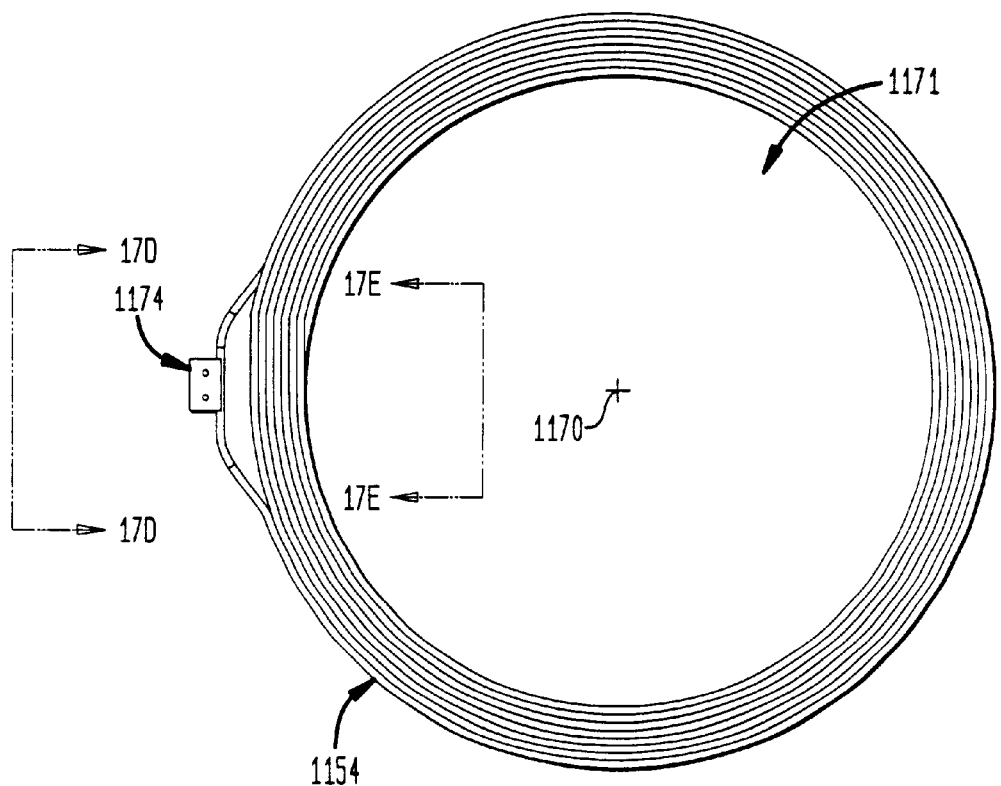
FIG. 17C is an end view of a coil according to the embodiment of FIGS. 17A and 17B.
Figure 17D:
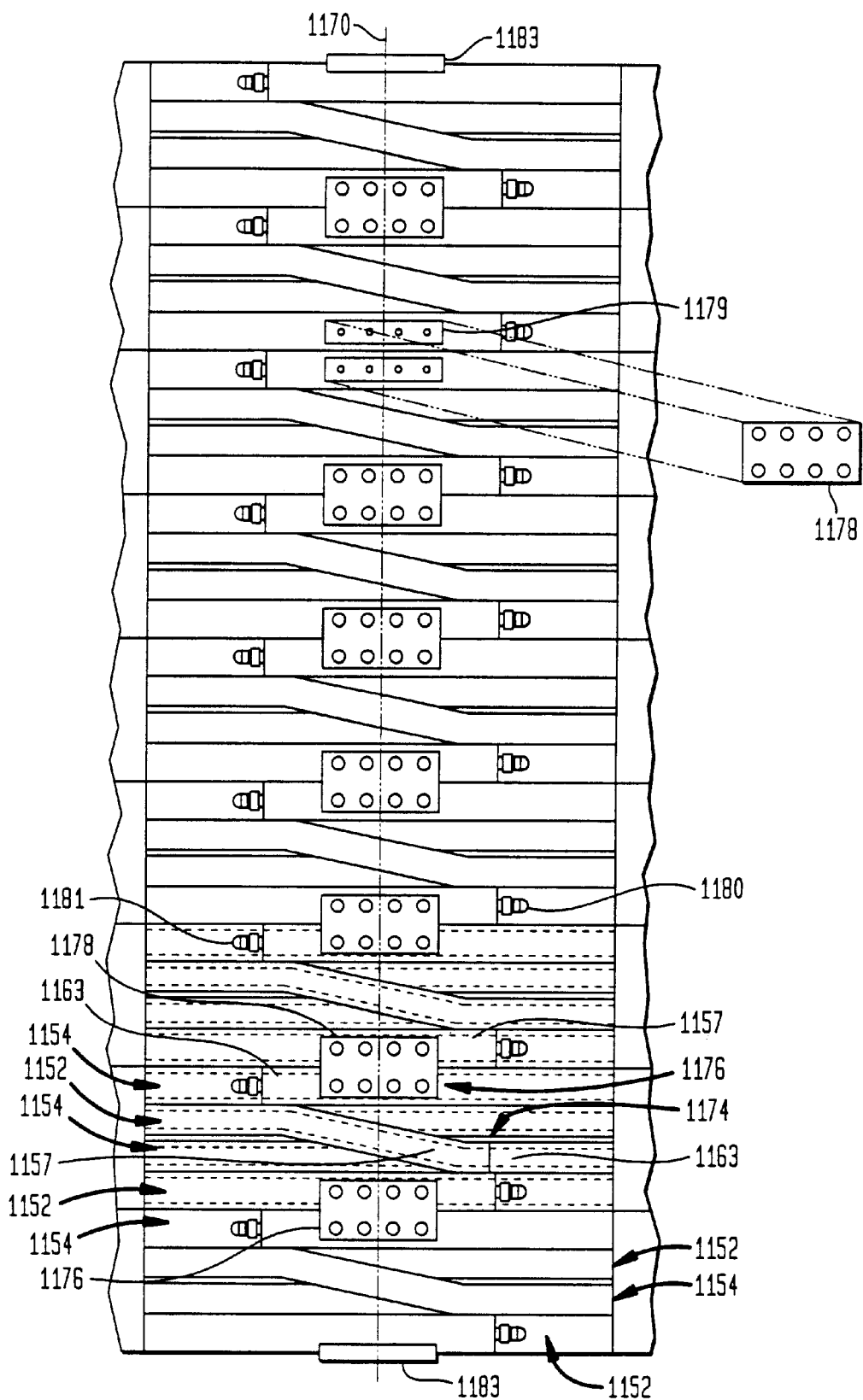
FIG. 17D is a fragmentary elevational view taken along line 17D—17D in FIG. 17C.
Figure 17E:
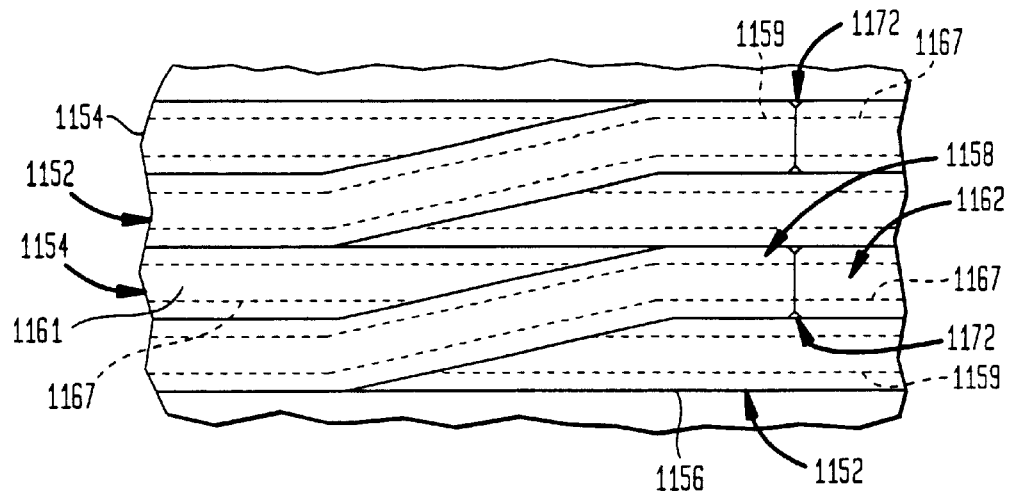
FIG. 17E is a fragmentary elevational view taken along line 17E—17E in FIG. 17C.

As best seen in FIGS. 17D and 17E, the inward windings and outward windings are stacked or superposed in alternating sequence, so that the axes of all of the coils lie on a common axis 1170. The inward windings and outward windings are arranged in alternating sequence within the stack. The stack thus defines a generally cylindrical coil with a central opening or bore 1171 (FIG. 17C). Adjacent coils within the stack are connected to one another at interior connections 1172 within central opening 1171 (FIG. 17E); at exterior connections 1174 of a first type on the outside of the stack and at exterior connections 1176 of a second type (FIG. 17B). At each interior connection, the inner end 1158 of an inward coil 1152 is joined to the inner end 1162 of the next-higher outward winding 1154 in the stack. At each such interior connection, the conductor 1156 of the inward coil is bent upwardly, out of the plane of the coil and soldered to the conductor 1161 of the outward winding. The solder joint is a butt joint arranged so that the bore 1159 of the inward winding communicates with the bore 1167 of the outward winding.

Each exterior connection 1174 of the first type (FIG. 17D) incorporates a similar soldered butt joint. At each such first-type exterior connection 1174, the outer end 1163 of an outward winding joins the outer end 1157 of the next higher inward winding 1152. At each first-type exterior connection 1174, the outer end of the inward winding is bent out of plane and the conductors of the windings are butted against one another and soldered so that the interior bores of the conductors communicate with one another.

At each exterior connection 1176 of the second type, the outer end 1163 of an outward winding is joined to the outer end 1157 of the next higher inward winding in the stack by a metallic joint plate 1178 bolted to the exterior of the windings. The winding ends desirably are provided with drilled and tapped pads 1179 soldered to the conductors at locations where the plates are to be installed. At the exterior connections 1176 of the second type, the bores of the conductors do not communicate with one another. Rather, the bores of the conductors are exposed on the exterior of the coil. The exposed ends provide fluid inlets 1180 and fluid outlets 1181. Hose fittings are provided at each such inlet and outlet.

Coil connectors 1183 are mounted on the ends of the top and bottom coils in the stack. All of the windings 1152 and 1154 are electrically connected in series with one another between the coil connectors 1183. Current passing into the coil at the outer end of the lowermost coil 1152 passes along the spiral winding to the inner end of the winding, and then passes to the next adjacent outward winding 1154. In the outward winding, the current flows from the inner end to the outer end, where it passes to the outer end of the next inward winding and so on. The current flows in all of the windings pass around the central axis 1170 in the same rotational direction, i.e., in the first rotational direction F seen in FIGS. 17A and 17B.

The windings connected to one another at the interior connections 1172 (FIG. 17E) and at the exterior connections 1174 of the first type have their bores connected with one another so as to form a continuous fluid path. However, the continuous fluid path does not extend through all of the windings. Rather, each such continuous fluid path extends through only four windings (two inward windings and two outward windings.) Stated another way, the bore of each winding is connected in one of the flow paths between one inlet and one outlet, but different windings are connected in different fluid flow paths. Each fluid flow path extends through less than all of the windings. This arrangement facilitates substantial fluid flow through the bores of the windings. The fluid flow resistance of a relatively short flow path for a few windings is only a fraction of the fluid flow resistance which would be encountered in a continuous flow path encompassing all of the windings. The ability to provide high coolant flows with reasonable coolant pressures greatly facilitates the task of maintaining the coil at a reasonable temperature in service. Moreover, the use of multiple fluid flow paths provide a cooling effect which is substantially uniform throughout the length of the coil. To provide a stable coil temperature in service, and thereby stabilize heat transfer to the ferromagnetic frame and the temperature of the frame in service, it is desirable to control the coil temperature as precisely as practicable. For example, the temperature and flow rate of the coolant should be stable. The temperature of the coolant can be controlled by a feedback control system. In one particularly preferred feedback control system, the coolant is chilled to a slightly greater extent than is required, and then heated by a balancing resistive heater in the coolant circuit. The feedback control system adjusts current flow to the balancing resistive heater to maintain the coolant temperature.

A further aspect of the invention further provides enhanced methods of coil fabrication. In constructing the coil of FIGS. 17A–17E, each winding can be fabricated by a relatively simple process of winding the conductor into the spiral and covering the conductor with insulation as, for example, by wrapping the conductor with tape as discussed above. Each winding is then joined to the next winding in the stack by straightforward soldering and bolting operations. Thus, the winding can be built easily, without great investments in tooling.

The coil configurations and fabrication methods discussed above can be varied. For example, each spiral winding may be frustoconical rather than planar. The frustoconical windings can be nested within one another when the windings are stacked during manufacture. Also, although it is preferred to stack the inward and outward windings in a simple alternating sequence, and to connect each winding with the immediately adjacent windings in the stack, this is not essential. For example, the windings can be stacked in pairs of outward windings and pairs of inward windings, the windings of each such pair being immediately adjacent to one another. Additional axially-extensive connectors can be provided to connect the windings electrically in inward-winding to outward-winding and outward-winding to inward winding sequence. More generally, the order of electrical connection does not necessarily correspond to the physical order of the windings.

Figure 18:
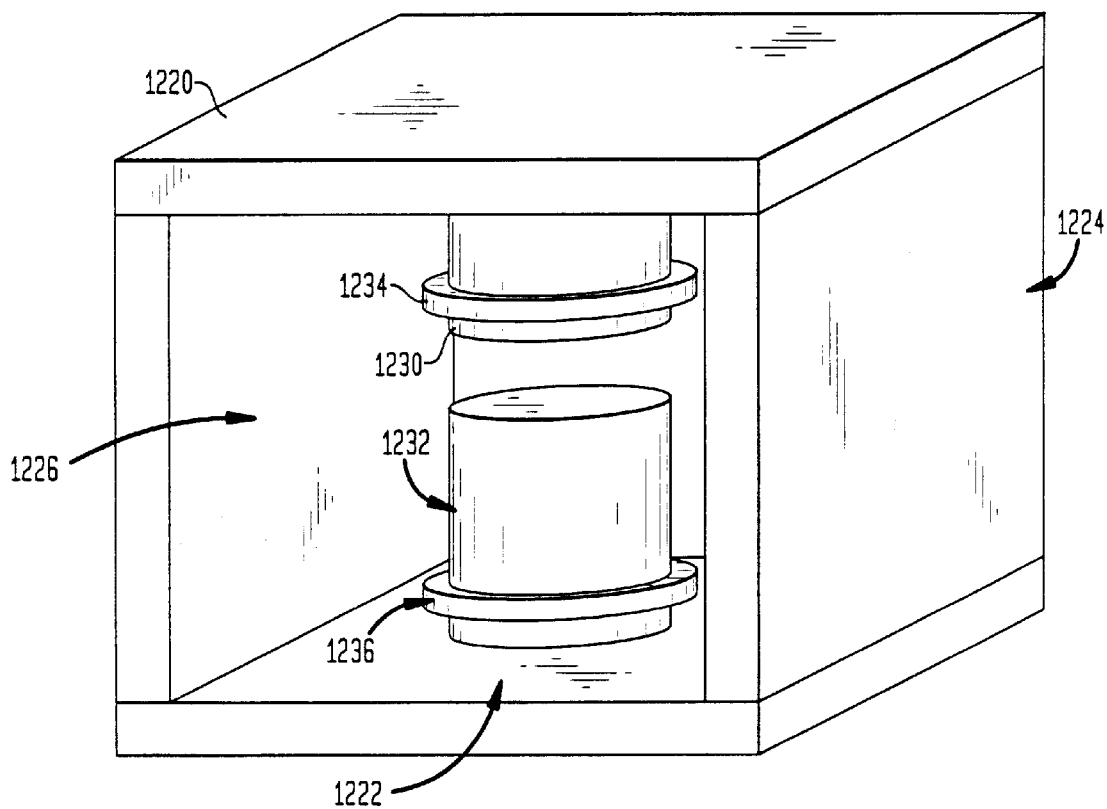
FIG. 18 is a diagrammatic perspective view of a magnet of in accordance with a further embodiment of invention.

The magnet depicted in FIG. 18 has a frame 1200 including pole supports 1220 and 1222 having connecting elements 1224 and 1226 similar to those discussed above. The frame includes upper and lower poles 1230 and 1232, which, similar to the apparatus depicted in FIG. 16, are generally cylindrical. Here, however, the coils 1234 and 1236 are superconducting coils formed as relatively narrow, ring-like structures having axial lengths substantially less than the axial length of the poles themselves. One coil 1234 is positioned close to the tip of the upper pole to promote field uniformity in the gap, whereas the other coil 1236 is positioned proximate to the lower pole support 1222, to provide enhanced access to the gap by a physician or technician standing within the working space. One advantage to this placement of the coils is that there is more working space available for the technician. Although coils 1234 and 1236 are shown in a single magnet, it should be appreciated that, in practice, the coils of a single magnet typically would be placed symmetrically. That is, either both coils would be close to the tips of the poles or both coils would be close to the pole supports. In a further variant, the coils can be mounted so that they can be moved along the poles to different positions to meet differing needs in service.

Figure 19:
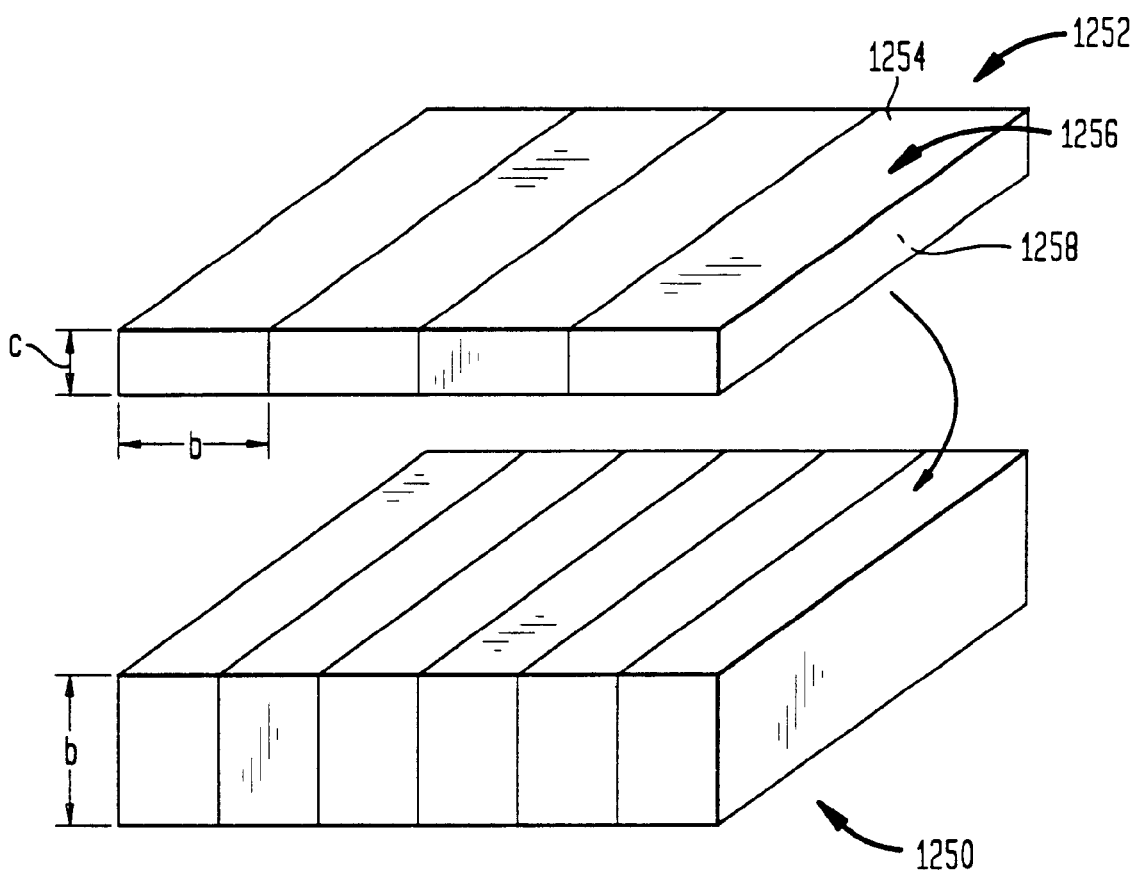
FIG. 19 is a diagrammatic perspective view depicting a plate fabrication process in accordance with a further embodiment of the invention.

The magnet structures discussed above include plate-like elements such as the connecting elements and pole supports. As depicted in FIG. 19, a composite plate 1250 having a thickness b can be fabricated from one or more starting plates 1252 having oppositely-directed major faces 1256 and 1258 a thickness c where c is less than b by cutting the plate into a plurality of strips 1254 each having a width equal to the desired thickness b of the composite plate. The strips are juxtaposed with one another so that the faces of the strips which originally constituted part of the major faces of the starting plate or plates confront one another. The strips can be joined with one another by a permanent method such as by welding or else can be held together by bolts or other conventional fasteners (not shown). Desirably, the long axes of the strips extend in the predominant direction of magnetic flux lines within the composite plate, so that the amount of flux passing between strips is minimal. Thus, where such a composite plate is used as a pole support, the long axes of the strips desirably extend between the connecting elements. Where the composite plate is used as a connecting element, the long axes of the strips desirably extend between the pole supports.

This method offers several significant advantages. Some preferred embodiments of the magnets discussed above use plates thicker than the thickest standard plates available from steel mills. For example, plates about 33 cm (13 inches) thick are used in some embodiments, whereas the thickest plates available as standard production items from steel mills are about 23 cm (9 inches) thick. While custom-rolled plates are available in thickness above 9 inches, they are more expensive and require considerable lead time, thus complicating production scheduling. Moreover, the ability to assemble the required plates from smaller parts facilitates shipment and installation of the magnet at customer premises such as at a hospital.

Figure 20:
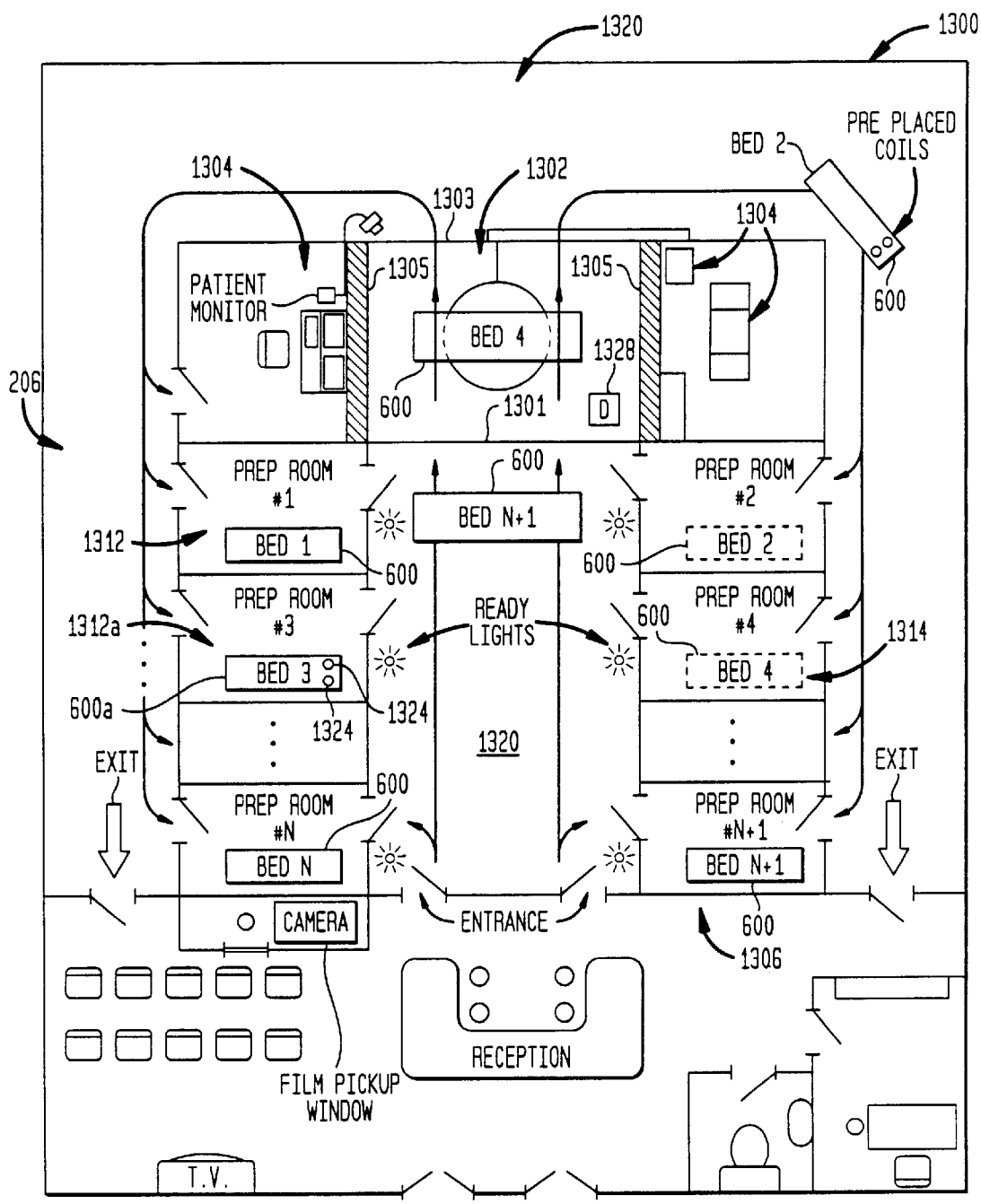
FIG. 20 is a top plan view depicting apparatus in accordance with another embodiment of the invention in conjunction with a building and other diagnostic apparatus.

As shown in FIG. 20, there is provided a diagnostic facility 1300, which includes the magnet such as those described in connection with FIGS. 1 through 6 or, preferably, as described with reference to FIG. 16. The magnet is not shown in detail but it is indicated at 1302. The magnet frame defines an open infeed side 1301 and an open outlet side 1303 extending between the ferromagnetic connecting elements 1305 of the magnet frame. Also included in the facility 1300 are the components of a magnetic resonance imaging apparatus other than the magnet, which components are indicated generally at 1304. These include the components discussed above, such as a computer for controlling the apparatus and for reconstructing images from data derived from the magnetic resonance signals, monitor, gradient coil driver and gradient coils and RF transmission and reception apparatus. The facility may also include devices 1328 for assisting in diagnostic procedures as, for example, devices for administering MRI contrast media or devices for affecting the patient in other ways. For example, the diagnostic devices 1328 may include devices for applying physical stimuli to the patient or administering diagnostic medications to the patient. These devices desirably are disposed within the working space of the magnet, so that a technician working on the patient can have access to these devices.

A plurality of patient-positioning devices or supports 600 are pre-positioned in a staging area 1306. Each device 600 may be a movable and adjustable bed as described above with reference to FIGS. 2–5. Staging area 1306 includes a plurality of preparation rooms 1312 disposed on opposite sides of an infeed corridor 1320 which extends to the infeed opening 1301 of the magnet frame. Each preparation room communicates with the infeed corridor 1320 via a doorway. The facility further includes an outfeed corridor 1322 communicating with the outfeed opening of the magnet frame and extending around the outer sides of the preparation rooms. Each preparation room communicates with the outfeed corridor at a doorway. In the particular embodiment shown, the outfeed corridor is generally U-shaped, but other configurations can be used as well, depending upon the layout of the facility.

The facility allows patient preparation and positioning so as to achieve an assembly-line effect. In FIG. 20, a device 600a is shown positioned in preparation room 1312a. A patient is loaded onto the device 600a and positioned on the device in an appropriate orientation for the procedure to be performed. The patient waits in position on device 600a until it is time for that patient to be moved into the patient-receiving gap of the magnet. In certain procedures, RF signals can be transmitted to the patient and/or received from the patient using a fixed RF antenna, permanently mounted near the gap of the magnet. In other procedures, it is desirable to use a local antenna disposed close to the region of the patient to be imaged. A local RF antenna 1324 for transmission and/or reception of RF signals may be positioned on the patient positioning device, in the desired relationship to the patient. Thus, the local RF antenna may be mounted on the patient's body while the patient and device 600 are in the preparation room. For example, portable RF antennas such as specialized RF antennas for monitoring particular body parts can be wrapped around a limb, head or other body part of the patient to provide optimized reception from these areas of the patient's body. Alternatively, the local RF antenna may be attached permanently or temporarily to the structure of device 600. For example, in systems for MRI examination of the breasts, some or all of the devices 600 may have pairs of loop-like breast coils surrounding indentations in the patient-supporting structure so that the patient can lie prone with the breasts positioned within the coils other devices 600 are positioned in additional rooms 1312. Again, the patient may be disposed on the devices 600 in these rooms, waiting his or her turn to be diagnosed by the MRI apparatus. As FIG. 20 shows, the number of devices 600 and rooms is only limited by the physical size of the facility 1300. Thus, the present invention contemplates N+1 devices and rooms.

In operation, each device 600, having a patient disposed thereon, is moved from a preparation room 1312 to the infeed corridor 1320 and is moved through the infeed corridor and into the magnet through infeed opening 1301. This movement may be manual or automated. The devices may be free moving on wheels, for instance, or on tracks or guide rails so that alignment is more readily achievable. While the first device is within the patient-receiving gap and while the patient on the first device 600 is being imaged, the next device 600 (with patient) from another room 1312 is moved into the corridor 1320 in a ready position. The first patient is imaged, the first device 600, with the patient thereon, is moved out of the magnet through outfeed opening 1303 and through outfeed corridor 1322 back to a preparation room 1312. The device 600 which was in the ready position is moved (with patient) through the infeed opening of the magnet into the patient-receiving gap of the magnet. This sequence of steps may be repeated again starting with the device in room 1312. Because devices 600 leave the magnet and return to the preparation rooms through the outfeed opening and outfeed corridor, they do not interfere with incoming devices 600. While each device 600 is disposed in the magnet, any local RF antenna carried on such device is operatively associated with the RF components of the MRI apparatus, either by physical connection through temporary cable connections or through free-space transmission of RF signals between the fixed antennas of the apparatus and the local RF antenna. The use of pre-positioned RF antennas carried with the patients into the magnet on the positioning devices 600 eliminates the need to delay imaging while setting up the RF antennas.

The devices can be moved into and out of the respective rooms in a sequential order, so that the device from a particular room 1312 is moved first, followed by the device from another particular room, and so on until all of the devices have been moved into the magnets. Preferably, however, the devices are moved into the ready position in the infeed corridor in an arbitrary fashion depending upon when the patient on the device is ready for imaging. A signaling system, such as ready lights 1326 visible in the infeed corridor, may be provided to indicate which patient is ready. In a further variant, each device is held in a preparation room until they it is advanced directly into the magnet. Because the devices are not held in the infeed corridor, patient privacy is enhanced. In any of these variants, a continual stream of patients can be imaged in succession. By maximizing patient throughput, the system minimizes the cost of each magnetic resonance procedure. This is particularly important where diagnostic procedures are to be performed as screening tests. While the foregoing discussion has centered on magnetic resonance imaging, it should be appreciated that the same considerations apply with respect to diagnostic applications of magnetic resonance other than imaging. For example, differences in magnetic resonance properties between normal and cancerous tissues make it possible to detect certain cancers by examining the magnetic resonance properties (e.g., the spin-spin and/or spin-lattice relaxation time or spectroscopic data) of a large body of tissue (e.g., a breast or limb or a portion of the breast or limb) as a whole, without attempting to reconstruct an image. If an abnormality is detected, the patient can then be subjected to imaging or other more expensive procedure.

Figure 21:
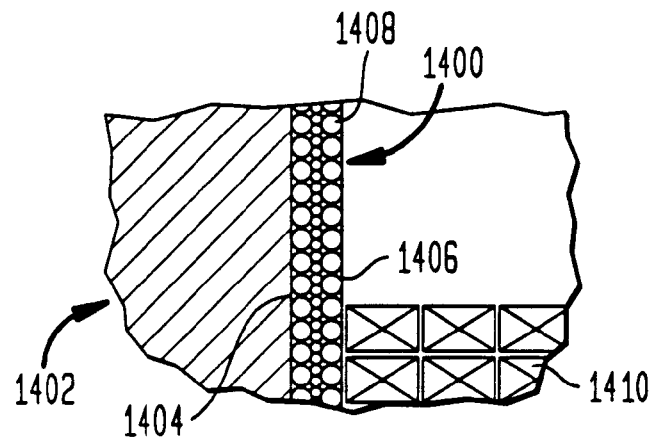
FIG. 21 is a fragmentary sectional view depicting a magnet in accordance with a further embodiment of the invention.

As seen in FIG. 21, a magnet frame may incorporate thermal insulation 1400 overlying surfaces of the ferromagnetic magnet frame 1402, including the side or circumferential surfaces of the poles so that the thermal insulation is disposed between the outer surface of each pole and the inner surface of the surrounding winding 1410. The thermal insulation in this region serves to reduce heat transfer from the coil to the pole. Thermal insulation desirably is also provided on other surfaces of the frame as, for example, on the connecting elements or vertical walls and pole supports or horizontal elements of the magnets discussed above. The thermal insulation can also be provided on other ferromagnetic magnet frames, such as on the frames shown and described in the aforementioned U.S. Pat. No. 5,754,085.

The particular thermal insulation depicted in FIG. 21 includes two layers 1404 and 1406 formed from a commercially available thermal insulation blanket sold under the trademark ASTROFOIL by Innovative Energy, Inc. of Lowell, Ind. The ASTROFOIL material includes two layers of aluminum foil laminated to the outside of a layer of polyethylene air bubble cushioning. The ASTROFOIL material has a nominal thickness of about 8 mm. A further layer of polyethylene air bubble cushioning 1408 is provided between the layers of ASTROFOIL material. Other types of thermal insulation can be utilized as well as, for example, foam polymers such as styrene foam, fibrous materials such as fibrous glass blankets and organic materials such as cork.

The thermal insulation helps to stabilize the temperature of the magnet frame. The thermal insulation on the pole surfaces reduces temperature changes in the poles due to heat transfer from the coils to the poles. The coil cooling arrangements discussed above contribute to this effect. Thermal insulation on other surfaces reduces the changes in frame temperature due to changes in the surrounding ambient temperature, and also helps the frame rise to an equilibrium temperature faster when power is applied to the main field coils. Both the mechanical and the magnetic properties of the magnet frame vary with the temperature of the frame. Stabilizing the frame temperature also helps to stabilize the magnetic properties of the frame and stabilizes the magnetic field provided in the magnet gap. Moreover, the changes in magnetic properties caused by temperature changes can include non-uniform field strength changes at different locations within the gap. By stabilizing the frame temperature, the insulation tends to reduce these temperature dependent non-uniformities. This, in turn, makes it easier to provide a highly uniform field. Conventional "shimming" or field correction devices can compensate for static non-uniformities, which do not change during operation of the unit, whereas more complex dynamic shimming devices are required to compensate for transient non-uniformities due to temperature effects on magnetic properties or mechanical dimensions. Thus, it is desirable to maintain the magnet frame at as close to a constant temperature as is practicable. Preferably, the average temperature of the magnet frame remains constant to within plus or minus 2 degrees Fahrenheit and more desirably to within plus or minus 1 degree Fahrenheit. Most desirably, the temperatures of individual elements of the frame are maintained constant with at least the same precision. For example, the temperatures of the poles should be maintained constant. Where the poles include pole stems, pole caps and shim bars, it is desirable to maintain these elements at substantially constant temperatures. Although the optimum effect is obtained by maintaining all of the elements of the frame at substantially constant temperatures, some benefit can be obtained even where the temperature of only some elements can be controlled with the desired precision.

Other features may be provided in the magnet to control the temperature of the frame. The frame may be provided with passages for a fluid heat transfer medium. Water or other conventional liquid heat transfer media, may be passed through these passages to a heat exchange device adapted to maintain the heat transfer medium at a constant temperature. Alternatively or additionally, the passages for the heat transfer medium may be provided in a thermally conductive plate or mass abutting the frame. In other, less preferred arrangements, the frame may be deliberately heated as, for example, by electrical resistance heaters mounted in heat transfer relation with the frame. This additional heating is provided in addition to incidental heating by the magnet coils. The additional heating devices, or a fluid cooling device, may be controlled by a feedback control circuit monitoring the temperature of the frame so as to maintain the frame at a substantially constant temperature. The thermal insulation and temperature control measures discussed above may also be used with other ferromagnetic magnet structures as, for example, the magnets shown in U.S. Pat. No. 5,754,085 and other magnets discussed in the aforementioned copending applications. In addition to the features of the magnet, it is desirable to maintain the frame in a well-controlled ambient temperature, e.g., in an ambient temperature which is constant to within approximately plus or minus 2 degrees Fahrenheit (1.1° C.) and more preferably within about 1 degree Fahrenheit (0.55° C.).

Figure 22:
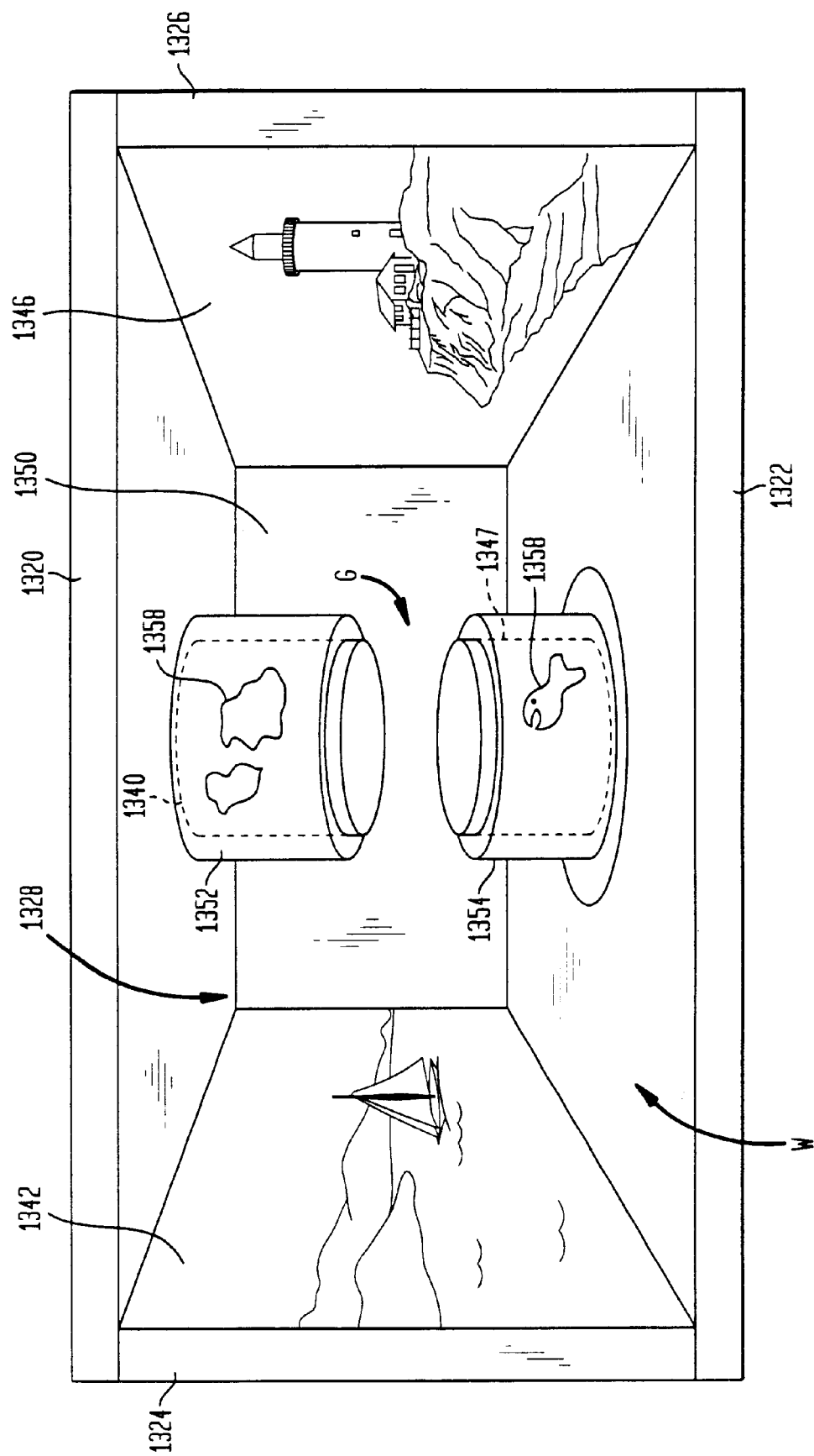
FIG. 22 is a perspective view depicting certain elements of a magnet in accordance with yet another embodiment of the invention.

The magnet depicted in FIG. 22 is generally similar to the magnets discussed above. The magnet of FIG. 22 has a pair of horizontal plate-like pole supports 1320 and 1322 and a pair of plate-like connecting elements 1324 and 1326 extending between the pole supports. Here again, the pole supports and connecting elements at least partially enclose a room 1328. As the interior surfaces of the pole supports and connecting elements are the bounding surfaces of the room, the connecting elements and pole supports themselves are disposed outside of the room. Generally cylindrical poles 1340 and 1342 project into the room from the floor and ceiling of the room. Here again, the room is large enough to accommodate both the poles and patient-receiving gap G together with a working space W sufficient to accommodate one or more physicians. As discussed above, the physicians in the working space will have essentially unrestricted access to the patient. Moreover, the entire magnet provides a non-claustrophobic experience to the patient. The magnet of FIG. 22 includes concealment structure in the form of surface ornamentation including pictures 1346 on interior surfaces of the room. In this case, the pictures are disposed on the interior surfaces of the connecting elements 1324 and 1326 defining side walls of the room as well as on a non-ferromagnetic, non-functional rear wall 1350. The magnet structure further includes pole covers 1352 and 1354 overlying the poles 1340 and 1342 and associated structures such as coils encircling the poles. The pole covers may also be provided with pictures 1358. Desirably the pictures on the interior surfaces of the room and on the pole covers from a unified scene, as for example, the marine scene depicted in FIG. 22 or some other type of outdoor scene. The scene desirably includes a depiction of a sky extending unto the ceiling of the room as, for example, in the inner surface of the upper pole support 1320 and may also include a natural-appearing earth tone or water tone on the floor, i.e., on the upper surface of lower pole support 1322. In the embodiment of FIG. 22, these concealing pictures are painted directly unto the surfaces of the metallic frame elements. However, the same pictures may be provided on other walls, floors or ceilings defining a room within the frame, as for example, on the wall coverings 68 discussed above with reference to FIG. 1, or on ceiling or floor coverings. In still further embodiments, the pictures may be dynamically provided as, for example, by a still projector, motion picture projector, projection television system, or computer-based projector which displays static or moving pictures on the exposed interior surfaces of the room. The pictures enhance the patient's experience during the procedure.

Figure 23:
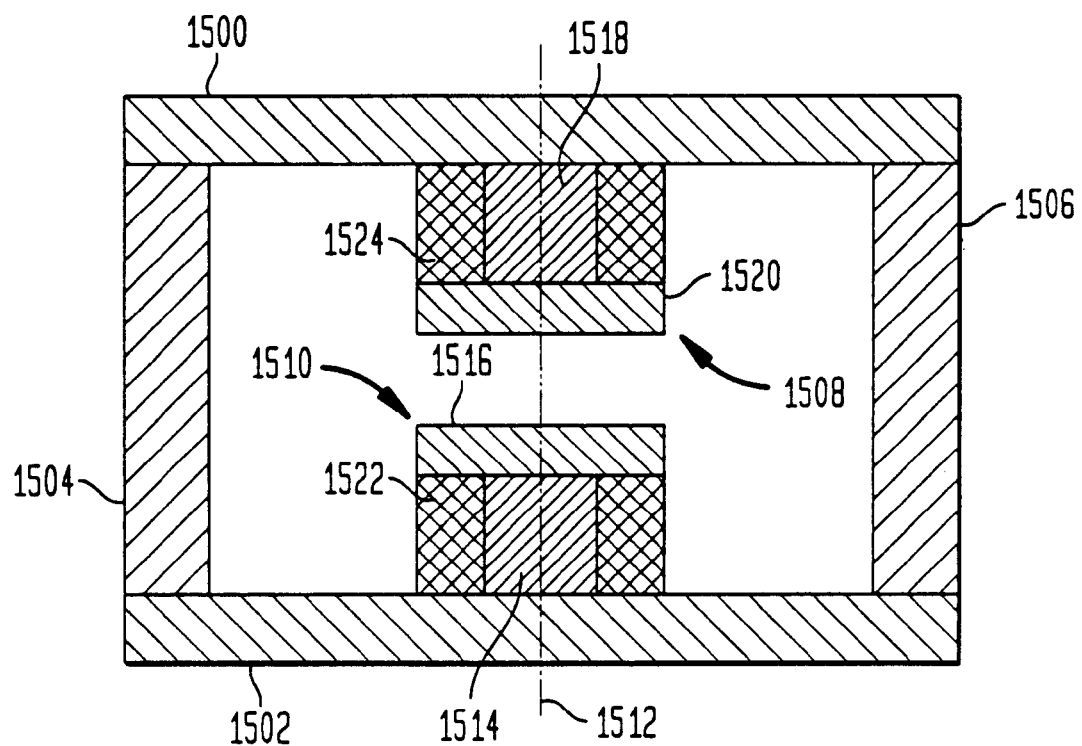
FIG. 23 is a diagrammatic sectional view depicting a magnet in accordance with yet another embodiment of the invention.

The magnet of FIG. 23 has a ferromagnetic frame including upper and lower pole supports 1500 and 1502 spaced apart from one another by connecting elements 1504 and 1506. The ferromagnetic frame further includes an upper pole 1508 and a lower pole 1510 connected to the pole supports and projecting towards one another along a polar axis 1512. The lower pole 1510 includes a ferromagnetic pole stem 1514 having relatively small dimensions transverse to the polar axis 1512 and a pole tip 1516 mounted to the pole stem at the end of the pole stem remote from the lower pole support. The pole tip has dimensions transverse to the polar axis greater than the corresponding dimensions of the pole stem. The upper pole includes a corresponding pole stem 1518 and pole tip 1520. The coil 1522 associated with lower pole 1510 encircles the pole step. Coil 1522 is disposed between the pole tip and the pole support, beneath the edge of the pole support. Stated another way, the coil lies at distances from the axis 1512 smaller than the distance from axis 1512 to the edge of the pole tip. In a variant of this approach, a portion of the coil is disposed between beneath the pole, whereas the remainder of the coil projects outwardly beyond the edge of the pole tip. These approaches reduce the size of the pole and coil assembly in directions transverse to the polar axis, and thus provide enhanced access to the patient. The upper coil 1524 may be arranged in the corresponding manner.

Numerous variations and combinations of the features discussed above can be utilized without departing from the present invention as defined by the claims. For example, in those embodiments where non-circular poles are employed, the pole may be generally elliptical or other shapes different from the generally rectangular poles discussed above. Also, the foregoing discussion has referred to the use of a single coil associated with each pole. As will be readily appreciated, more than one coil can be provided for each pole. Accordingly, the foregoing description of the preferred embodiments should be taken by way of illustration rather than by way of limitation of the invention as claimed.

What is claimed is:

1. A resistive coil for a magnetic resonance imaging static field magnet comprising a plurality of spiral windings extending around an axis, each of said plurality of windings having an inner end adjacent the axis, an outer end remote from the axis and a conductor extending in multi-turn spiral between said inner end and said outer end, said plurality of windings including one or more outward windings and one or more inward windings, turns of each outward winding being arranged such that a point moving along the turns in a first direction of rotation about the axis moves from said inner end towards said outer end, turns of each said inward winding being arranged so that a point moving along the turns in said first direction of rotation about the axis moves from said inner end towards said outer end, said plurality of windings being stacked, one above the other along said axis, said plurality of windings being electrically connected in series with one another, the electrical connections including one or more interior connections, said inner end of one of said inward windings being connected to said inner end of one of said outward windings at each such interior connection.

2. A coil as claimed in claim 1 wherein the electrical connections include one or more exterior connections, said outer end of one of said outward windings being connected to said outer end of one of said inward windings at each said exterior connection.

3. A coil as claimed in claim 2 wherein said inward windings and said outward windings are arranged in alternating sequence along said axis, and wherein said interior connections and said exterior connections are also arranged in alternating sequence along said axis.

4. A coil as claimed in claim 2 wherein said conductors of said windings are tubular so that each said winding has a bore extending between its inner end and its outer end, said coil further including a plurality of coolant ports, said coolant ports including one or more coolant inlets and one or more coolant outlets connected to said bores of said windings for passing coolant through said windings.

5. A coil as claimed in claim 4 wherein said bores of at least some of said windings are connected to one another at at least some of said connections.

6. A coil as claimed in claim 5 wherein said coolant ports are arranged so that said bore of each said winding is connected in a fluid flow path between one of said inlets and one of said outlets, each said fluid flow path extends through less than all of said windings, and different ones of said windings are connected in different fluid flow paths.

7. A coil as claimed in claim 6 wherein, at at least some of said exterior connections, said bores of said windings which are electrically connected at said exterior connection are not connected to one another and said bores are connected to said coolant ports.

8. A magnet for resonance imaging comprising at least two coils as claimed in claim 1 and a ferromagnetic frame including a pair of ferromagnetic poles projecting along a polar axis defining a patient-receiving gap therebetween, said poles having proximal ends remote from said gap and tips bounding said gap, said frame further including a ferromagnetic flux return structure extending between poles, said coils encircling said poles.

* * * * *